US010076353B2

(12) United States Patent
Kawaura et al.

(10) Patent No.: US 10,076,353 B2
(45) Date of Patent: Sep. 18, 2018

(54) MEDICAL DEVICE

(71) Applicant: TERUMO KABUSHIKI KAISHA, Shibuya-ku, Tokyo (JP)

(72) Inventors: Masakatsu Kawaura, Sunnyvale, CA (US); Nao Yokoi, Sunnyvale, CA (US); Shigeki Ariura, Ebina (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 191 days.

(21) Appl. No.: 14/868,945

(22) Filed: Sep. 29, 2015

(65) Prior Publication Data
US 2016/0015414 A1    Jan. 21, 2016

Related U.S. Application Data

(63) Continuation of application No. PCT/JP2013/059890, filed on Apr. 1, 2013.

(51) Int. Cl.
*A61B 17/34*    (2006.01)
*A61B 17/3209*    (2006.01)
(Continued)

(52) U.S. Cl.
CPC ........ *A61B 17/3209* (2013.01); *A61B 17/062* (2013.01); *A61B 17/06109* (2013.01);
(Continued)

(58) Field of Classification Search
CPC ... A61B 17/3209; A61B 17/42; A61B 17/062; A61B 17/06109; A61B 17/34;
(Continued)

(56) References Cited

U.S. PATENT DOCUMENTS 5,544,664 A    8/1996    Benderev et al.
6,911,003 B2 *    6/2005    Anderson .......... A61B 17/0401
                                                        600/30
(Continued)

FOREIGN PATENT DOCUMENTS

JP    9-248306 A    9/1997
JP    2001-511686 A    8/2001
(Continued)

OTHER PUBLICATIONS

International Search Report (PCT/ISA/210) dated Jun. 4, 2013, by the Japanese Patent Office as the International Searching Authority for International Application No. PCT/JP2013/059890.

*Primary Examiner* — Victor Nguyen
(74) *Attorney, Agent, or Firm* — Buchanan Ingersoll & Rooney PC

(57) ABSTRACT

A medical device is disclosed, which includes a urethral insertion member and a vaginal insertion member which are inserted into the urethra and the vagina positioned adjacent each other, respectively, with a biological tissue interposed therebetween, a puncture needle disposed for movement for passing the biological tissue between the urethra and the vagina, a supporting member which supports the puncture needle for movement and supports the urethral insertion member and the vaginal insertion member thereon, a dissection portion which dissects, when the puncture needle moves, the biological tissue in accordance with the movement, and a restriction mechanism which restricts the dissection portion such that the direction in which the dissection portion dissects the biological tissue is fixed with respect to the urethral insertion portion and the vaginal insertion portion.

20 Claims, 26 Drawing Sheets

(51) Int. Cl.
*A61F 2/00* (2006.01)
*A61B 17/06* (2006.01)
*A61B 17/062* (2006.01)
*A61B 17/00* (2006.01)
*A61B 17/32* (2006.01)
*A61B 17/42* (2006.01)

(52) U.S. Cl.
CPC ............ *A61F 2/0045* (2013.01); *A61B 17/42* (2013.01); *A61B 2017/00805* (2013.01); *A61B 2017/0608* (2013.01); *A61B 2017/06019* (2013.01); *A61B 2017/06042* (2013.01); *A61B 2017/06076* (2013.01); *A61B 2017/320052* (2013.01); *A61F 2220/0033* (2013.01)

(58) Field of Classification Search
CPC . A61B 2017/0042; A61B 2017/320052; A61F 2/00; A61F 2/0045
See application file for complete search history.

(56) References Cited

U.S. PATENT DOCUMENTS

| 2003/0171644 | A1 | 9/2003 | Anderson et al. |
| 2008/0171905 | A1* | 7/2008 | Anderson ............ A61F 2/0036 600/29 |
| 2012/0010627 | A1 | 1/2012 | Watschke et al. |

FOREIGN PATENT DOCUMENTS

| JP | 2005-514967 A | 5/2005 |
| JP | 2006-517115 A | 7/2006 |
| JP | 2010-099499 A | 5/2010 |
| WO | WO 98/35606 A2 | 8/1998 |
| WO | WO 02/098322 A1 | 12/2002 |
| WO | WO 2004/016196 A2 | 2/2004 |

* cited by examiner

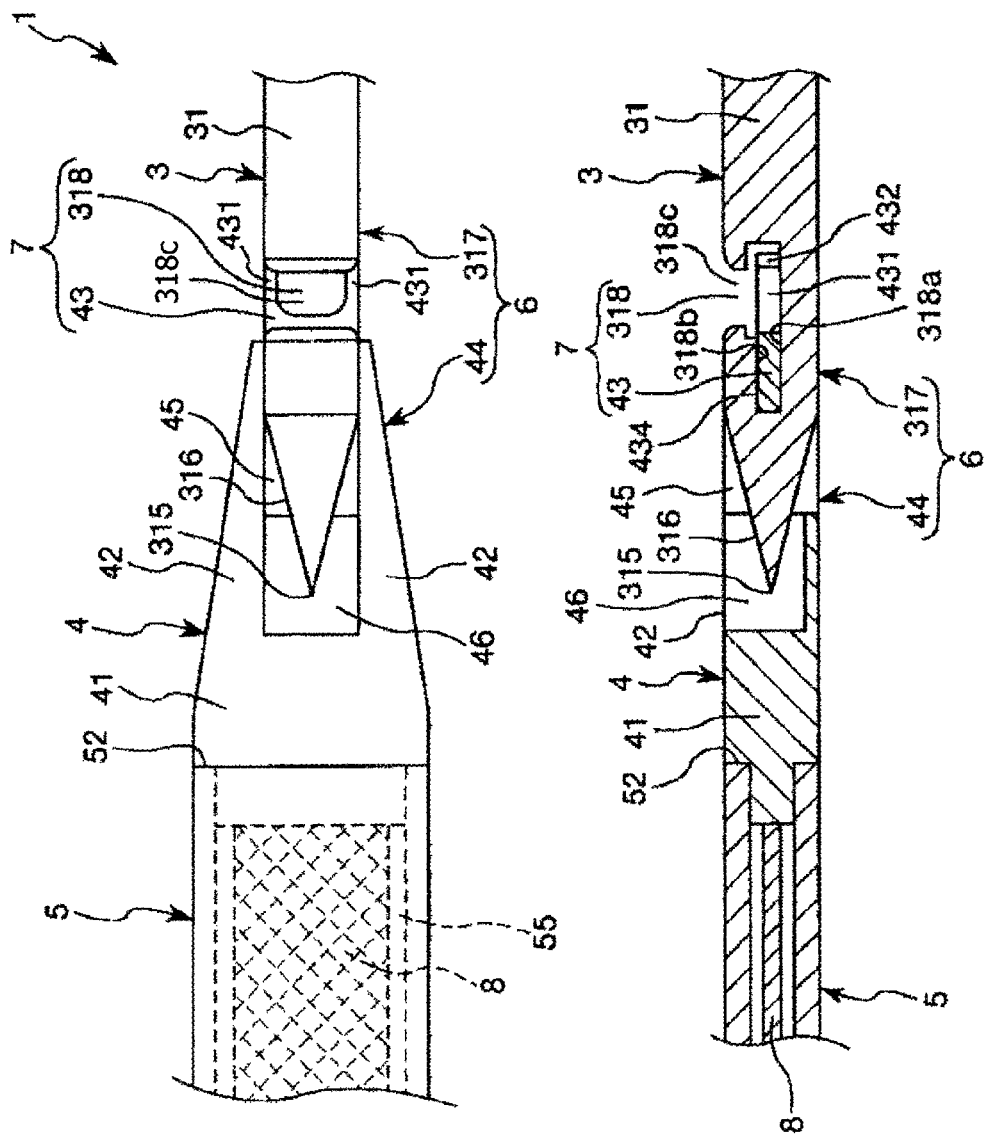

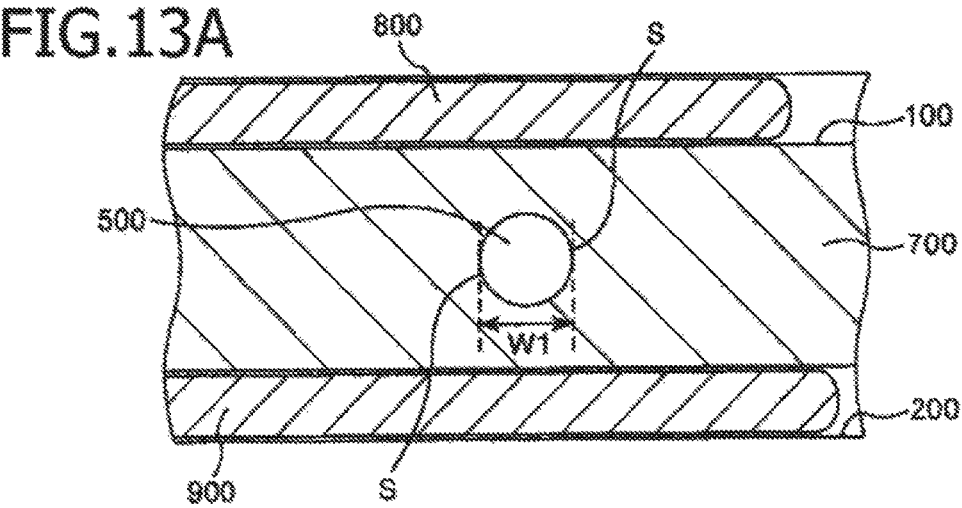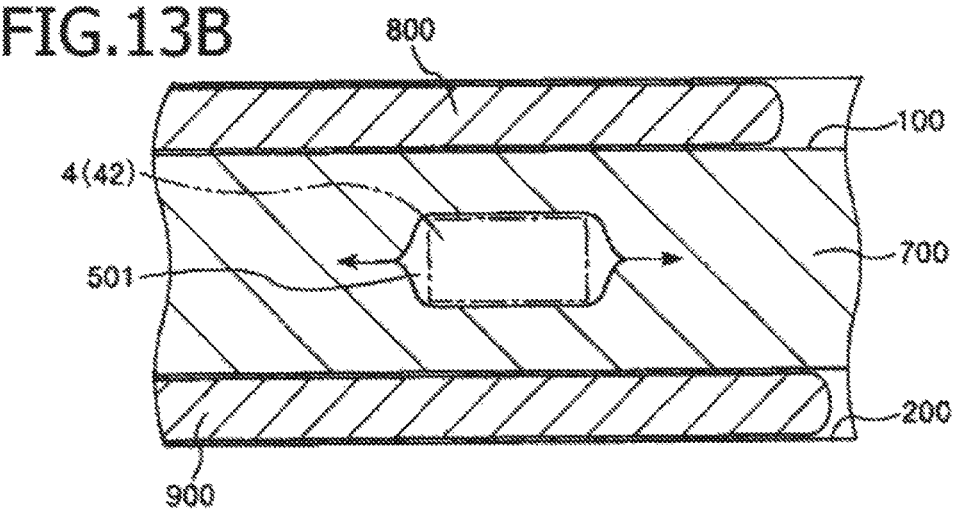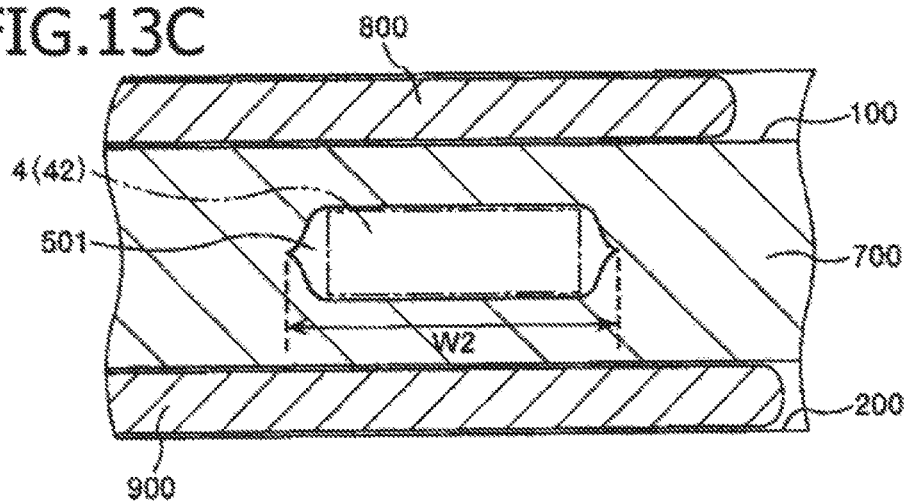

MEDICAL DEVICE

CROSS-REFERENCES TO RELATED APPLICATIONS

This application is a continuation of International Application No. PCT/JP2013/059890 filed on Apr. 1, 2013, the entire content of which is incorporated herein by reference.

TECHNICAL FIELD

The present disclosure generally relates to a medical device.

BACKGROUND DISCUSSION

If a person suffers from urinary incontinence, for example, from stress urinary incontinence, then urine leakage can occur when abdominal pressure is applied during normal movement or by laughing, coughing, sneezing or the like. This can be caused, for example, by a fact that pelvic floor muscles which are muscles which support the urethra are loosened by birth or the like.

For the treatment of urinary incontinence, surgical therapy is effective, and for example, an elongated tape-shaped (elongated) implant called "sling" is used. The sling is dwelled into the body to support the urethra (for example, refer to Japanese Patent Laid-Open No. 2010-99499). In order to indwell the sling, the operator incises the vagina wall with a scalpel, dissects a biological tissue between the urethra and the vagina and communicates the dissected region and the outside through an obturator foramen of the pelvis using a puncture needle to form a puncture hole. Then, the sling is indwelled into the body using such a puncture hole as just described.

However, if the vaginal wall is incised, the sling may be exposed to the inside of the vagina through a wound caused by the incision or that complications such as an infection from the wound can occur. Further, since the vaginal wall is incised, the invasion is relatively significant and the burden on the patient is relatively high. Further, the urethra or the like may be damaged by a scalpel during the manipulation by the operator, and the operator may be injured, for example, an operator's finger may be cut by a scalpel.

For example, in order to indwell a sling in a predetermined direction, it can be necessary to dissect the biological tissue by a considerably greater amount than the width of the sling. Therefore, there is a drawback that the burden on the patient is relatively significant.

SUMMARY

A medical device is disclosed by which, when an elongated implant is to be indwelled in a predetermined direction into a living body, the indwelling operation can be carried out readily and with certainty and which imposes less burden on the patient and is high in safety of the patient and high also in safety of the operator.

A medical device is disclosed, which includes an insertion portion configured to be inserted into a biological lumen, an elongated body provided for movement and configured to pass a biological tissue, a supporting member configured to support the elongated body for movement thereon and support the insertion portion thereon, a dissection portion (or separation unit) configured to dissect (or separate), when the elongated body moves, the biological tissue in accordance with the movement of the elongated body, and a restriction mechanism configured to restrict the dissecting portion such that a direction in which the dissecting portion dissects the biological tissue is fixed with respect to the insertion portion.

According to an exemplary embodiment, the direction in which the dissection portion dissects the biological tissue is parallel at least part thereof to the insertion portion.

According to an exemplary embodiment, the medical device may be configured such that the insertion portion is a urethral insertion portion configured to be inserted into the urethra; the elongated body is disposed for turning motion; and a direction in which the dissection portion dissects when the biological tissue on the remote side of the urethral insertion portion with respect to a center axis of turning motion of the elongated member is to be dissected is a parallel direction to the urethral insertion portion.

According to an exemplary embodiment, the medical device may be configured such that the insertion portion includes a urethral insertion portion configured for insertion into the urethra and a vaginal insertion portion configured for insertion into the vagina; the elongated body is disposed for turning motion; and a direction in which the dissection portion dissects when the biological tissue on the near side of the vaginal insertion portion with respect to a center axis of turning motion of the elongated member is to be dissected is a parallel direction to the urethral insertion portion.

According to an exemplary embodiment, the insertion portion preferably has a first insertion portion and a second insertion portion configured to be inserted into two biological lumens positioned adjacent each other with the biological tissue interposed between the two biological lumens, and a direction in which the dissection portion dissects the biological tissue between the first insertion portion and the second insertion portion is a parallel direction to at least one of the first insertion portion and the second insertion portion.

According to an exemplary embodiment, the medical device may be configured such that the first insertion portion is a urethral insertion portion configured for insertion into the urethra; the second insertion portion is a vaginal insertion portion configured for insertion into the vagina; and the direction in which the dissection portion dissects the biological tissue between the urethral insertion portion and the vaginal insertion portion is a parallel direction to at least one of the urethral insertion portion and the vaginal insertion portion.

According to an exemplary embodiment, the medical device preferably further includes a medical tube configured to be inserted into the biological tissue in an assembled state in which the medical tube is inserted in and assembled to the elongated body.

According to an exemplary embodiment, the medical device may be configured such that the medical tube and the elongated body have, at least at part thereof in a longitudinal direction, a flattened portion having a flattened transverse sectional shape such that the flattened portions of the medical tube and the elongated body in the assembled state overlap with each other to exhibit a function as the restriction mechanism.

According to an exemplary embodiment, the medical device may be configured such that the medical tube has, at a distal end portion thereof, a needle tip portion configured to puncture the biological tissue.

According to an exemplary embodiment, the medical device preferably further includes a medical tube having an elongated shape and configured to be inserted into a living body, and a guide member configured to guide the medical tube when the medical tube is to be pulled off from the biological tissue.

According to an exemplary embodiment, the medical device may be configured such that the elongated body has a curved portion curved in an arc, and the guide member has a curved face which has a curved face curved in a direction same as the curved portion of the elongated body and is configured to abut with the medical tube.

According to an exemplary embodiment, the medical device may be configured such that the elongated body has a curved portion curved in an arc; the medical tube has an end opening open to a distal end thereof; and the guide member has an elongated shape curved in a direction same as a direction of the curved portion and is configured at a distal end portion thereof from a hard member configured to be inserted into the end opening.

According to an exemplary embodiment, the dissection portion preferably has a flattened shape and has a tapering portion whose width gradually decreases in a forward direction of movement of the dissection portion.

According to an exemplary embodiment, the medical device further includes a pressing member configured to press the biological tissue while the elongated body passes the biological tissue.

According to an exemplary embodiment, the elongated body is disposed for turning motion and has a curved portion curved in an arc and a shaft portion having a center axis at the center of the arc, and the shaft portion is inclined by 3 to 60 degrees with respect to a longitudinal direction of the insertion portion.

With the medical device according to the present disclosure, when an elongated implant is to be embedded into a living body such that it is directed in a predetermined direction, the embedding operation can be carried out readily and with certainty, and the burden on the patient is light. Further, the safety of the patient and operator can be relatively high.

For example, where the medical device of the present disclosure is used for treatment of urinary incontinence of a female, when an elongated implant for treatment of urinary incontinence is to be embedded, incision of the vaginal wall is unnecessary, and the implant can be embedded by a manipulation of a relatively low invasiveness. Further, such a situation that the implant is exposed to the inside of the vagina through a wound caused by incision as in the case in which the vaginal wall is incised or that such complications as infection from the wound can be prevented, and which is relatively safe, and the implant can be embedded with relative certainty.

For example, since the biological tissue can be dissected with a predetermined width by the dissection portion, the implant can be embedded with relative certainty by a manipulation of a relatively low invasiveness.

Further, the puncture needle and the connector (dissection portion) can be connected to each other such that the positional relationship of the puncture needle and the connector in the rotational direction around the axis is fixed. Further, in this connection state, rotation of the connector around the axis with respect to the puncture needle is restricted. Therefore, the implant can be embedded such that the direction of the implant can be fixed with respect to the insertion portion.

A method is disclosed of forming a path in biological tissue, the method comprising: inserting an insertion portion into a biological lumen; moving an elongated body past a biological tissue; supporting the elongated body and the insertion portion on a supporting member; dissecting, when the elongated body moves, the biological tissue in accordance with the movement of the elongated body with a dissection portion; and restricting the dissection portion such that a direction in which the dissection portion dissects the biological tissue is fixed with respect to the insertion portion.

Further, since the operator need not carry out the incision, the fingertip of the operator can be prevented from being damaged, for example, by a scalpel.

BRIEF DESCRIPTION OF THE DRAWINGS

FIGS. 11A and 11B are a plan view and a cross sectional view, respectively, of the medical device depicted in FIG. 10 in a connection state in which a puncture needle and a connector of the medical device are connected to each other;

FIGS. 13A, 13B, and 13C are cross sectional views depicting a process in which a secondary threading hole is formed by a dissection portion;

DETAILED DESCRIPTION

In the following, a medical device of the present disclosure is described in detail with reference to preferred embodiments of the present disclosure depicted in the accompanying drawings.

First, a medical device according to a first exemplary embodiment of the present disclosure is described with reference to FIGS. 1 to 14B.

It is to be noted that, in the following description, an upper side in FIGS. 1 to 9 and 13 is referred to as "upper" side while a lower side is referred to as "lower" side. Further, a needle tip end side is referred to as "distal end" side while the opposite side is referred to as "proximal end" side.

Further, while a puncture needle 31 and a connector assembly 2 are actually curved as hereinafter described, in FIGS. 10 to 12C, they are depicted in a substantially linear shape (this similarly applies also to views depicting the other embodiments).

Figure 3:
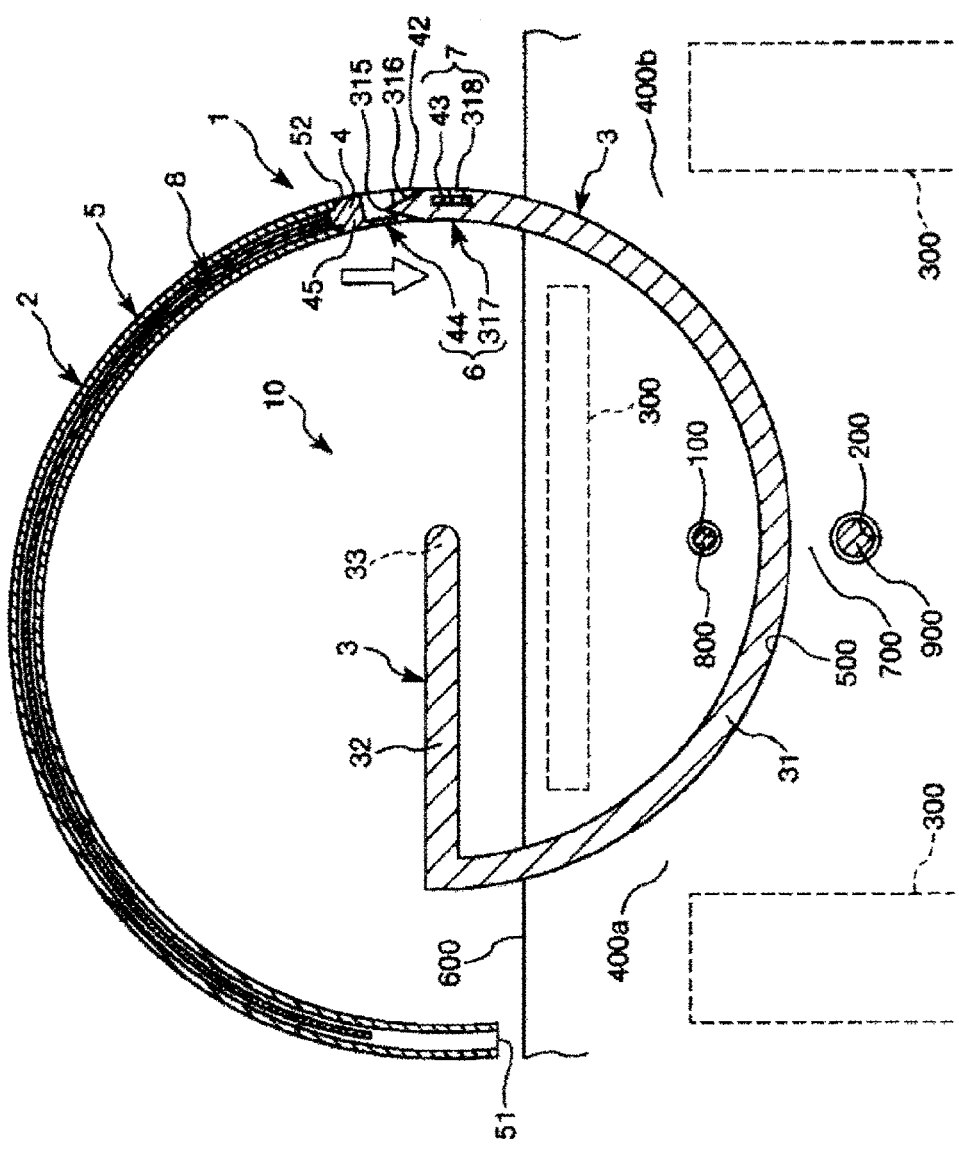
Figure 4:
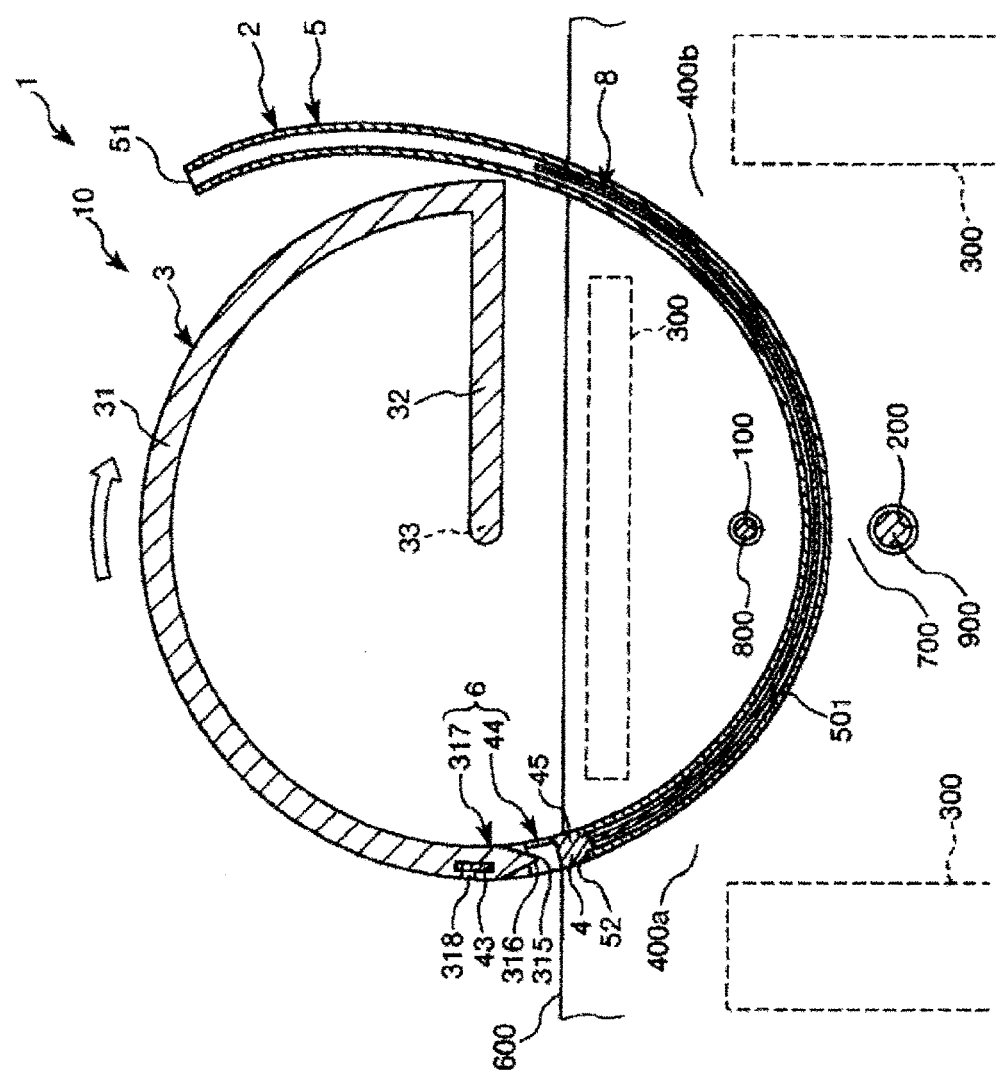

As depicted in FIGS. 3 and 4, a medical device 1 can include a puncture device 10, an connector assembly 2 having an implant 8, a connection mechanism 6 capable of connecting the puncture device 10 and the connector assembly 2 to each other, and a rotation restriction mechanism (restriction mechanism) 7. The medical device 1 can be used to embed the implant 8 for treatment of urinary incontinence of a female, for example, for example, for treatment of urinary incontinence, into a living body. In the following, the configuration of the components is described.

As depicted in FIGS. 1 to 4 and 9, the puncture device 10 can include a puncture member (elongated body) 3, a supporting member 20 which supports the puncture member 3 for turning motion (movement), a urethral insertion member (urethral insertion portion) (first insertion portion) 800 in the form of a bar which is inserted into the urethra (living body lumen) 100, and a vaginal insertion member (vaginal insertion portion) (second insertion portion) 900 in the form of a bar which is inserted into the vagina (living body lumen) 200.

The puncture member 3 has a puncture needle 31 for puncturing a biological tissue 700, a shaft portion 33, and a connection portion 32 for connecting the puncture needle 31 and the shaft portion 33 to each other.

The puncture needle 31 has a sharp needle tip (needle tip portion) 315 at the distal end of the puncture needle 31 and a curved portion curved in an arc centered at the shaft portion 33. Further, the puncture needle 31 has a circular transverse sectional shape. The axial line of the puncture needle 31 and the axial line of the shaft portion 33 have a twisted positional relationship to each other. Consequently, when the puncture member 3 turns around the axis of the shaft portion 33, the needle tip 315 of the puncture needle 31 moves along the arc in a plane perpendicular to the axial line of the shaft portion 33, for example, within a plane having a normal provided by the axial line of the shaft portion 33. It is to be noted that the needle tip 315 need not necessarily be sharp, but, for example, may be rounded.

Further, the central angle of the arc of the puncture needle 31 is not limited particularly and can be suitably set in accordance with various conditions. However, the central angle can be set such that, when the biological tissue 700 is punctured by the puncture needle 31, such a primary threading hole 500 having an arcuate shape as hereinafter described is formed in the biological tissue 700. Such a central angle as just described preferably can be, for example, 150 to 270 degrees, more preferably is 170 to 250 degrees, and most preferably is 190 to 230 degrees.

Further, while, in the present embodiment, the needle tip 315 of the puncture needle 31 is directed to a counterclockwise direction in FIGS. 1 to 4, the needle tip 315 is not limited to this but may be directed to a clockwise direction.

Further, the puncture needle 31 has a tapering portion 316 formed thereon such that the outer diameter thereof gradually increases in a direction from the needle tip 315 toward the proximal end. Consequently, if the puncture needle 31 is turned in the direction of an arrow mark in FIG. 2 (in the counterclockwise direction), then as the needle tip 315 punctures the biological tissue 700, the needle tip 315 can dissect the punctured portion of the biological tissue 700 so as to be gradually split in a direction in which the urethra 100 and the vagina 200 are spaced away from each other. The primary threading hole 500 is formed thereby. Since the primary threading hole 500 is formed by the puncture needle 31 having a circular transverse sectional shape, it has a substantially circular transverse sectional shape (refer to FIG. 13A).

In accordance with an exemplary embodiment, if the biological tissue 700 is punctured and then the puncture needle 31 is turned, in a state in which the needle tip 315 is exposed to the upper side from a living body surface 600 after completion of the puncture (this state is hereinafter referred to as "puncture completion state"), in the opposite direction (clockwise direction), then the puncture needle 31 is pulled off from within the living body.

The puncture needle 31 is configured for back and forth movement in this manner. It is to be noted that, in the following description, the route when the puncture needle 31 turns in the counterclockwise direction is referred to as "forward path" and the route when the puncture needle 31 turns in the clockwise direction is referred to as "return path."

While the transverse sectional shape of the puncture needle 31 in the present embodiment is a circular shape, it is not limited to this and may be a non-circular shape. Further, while the puncture needle 31 in the present embodiment is a solid needle, it is not limited to this and may be a hollow needle.

It is to be noted that the puncture needle 31 may have a linear portion and may have a linear shape over an overall length thereof in the lengthwise direction.

Such a puncture needle 31 as described above has, at the needle tip (distal end portion) 315 thereof, a connection portion (first connection portion) 317. This connection portion 317 has a recessed portion (first concave portion) 318 formed on the proximal end side of the tapering portion 316. The recessed portion 318 is open not only to the front face side of the plane of FIG. 10 but also to the opposite side in the upward and downward direction in FIG. 10. Further, the inside of the recessed portion 318 is formed to extend to the distal end side farther than an entrance 318c of the recessed portion 318 and to the proximal end side farther than the entrance 318c of the recessed portion 318. For example, the inside of the recessed portion 318 is formed wider to the distal end side and the proximal end side than the entrance 318c of the recessed portion 318. Further, a bottom face 318a and a top face 318b in the recessed portion 318 are flat faces. The recessed portion 318 serves also as a first rotation restriction portion.

The shaft portion 33 serves as a rotational shaft of the puncture member 3 (puncture needle 31) and is provided for rotation on the supporting member 20.

Figure 9:
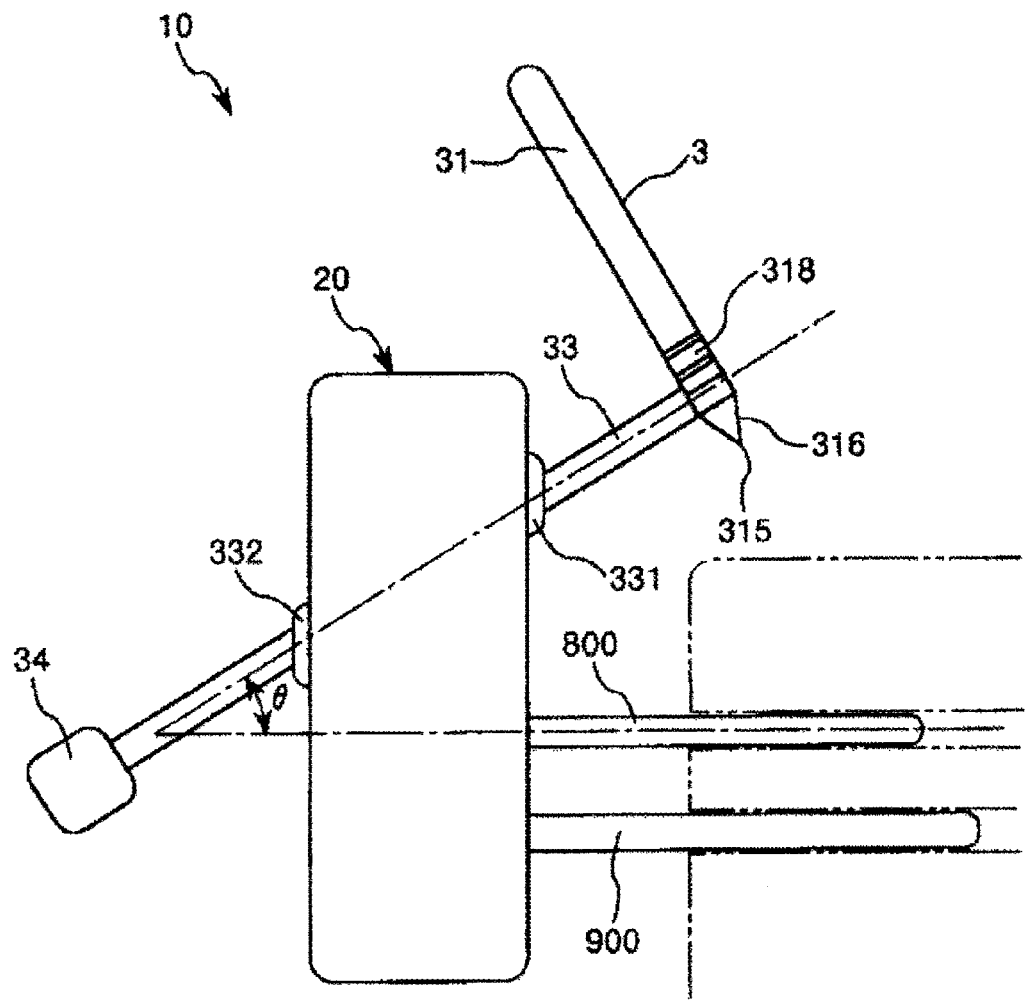
FIG. 9 is a side elevational view of the medical device as viewed in a direction indicated by an arrow mark A in FIG. 1.

As depicted in FIG. 9, the shaft portion 33 extends in the leftward and rightward direction in FIG. 9 through the supporting member 20. Further, flanges 331 and 332 are formed at a distal end side portion and a proximal end side portion of the shaft portion 33 through the supporting member 20, respectively. The flanges 331 and 332 restrict movement of the shaft portion 33 in the axial direction with respect to the supporting member 20.

Further, as depicted in FIG. 9, the shaft portion 33 can be inclined with respect to the axial line of the urethral insertion member 800 or the vaginal insertion member 900 such that the distance between the axial line of the shaft portion 33 and the axial line of the urethral insertion member 800 or the vaginal insertion member 900 increases toward the right in FIG. 9. The inclination angle θ between the shaft portion 33 and the axil line of the urethral insertion member 800 or the vaginal insertion member 900 can be, for example, 20 to 60 degrees, preferably 30 to 45 degrees, more preferably 35 to 40 degrees, and most preferably 37.5 degrees. With the inclination angle θ, puncture of the puncture needle 31 can be carried out readily and a smaller puncture distance can be achieved.

In accordance with an exemplary embodiment, for example, where the inclination angle θ is set so as to be within the range described above, the puncture needle 31 can grasp the left and right obturator foramen 400a and 400b of the pelvis widely in plane, and a wide space can be assured for a puncture space of the puncture needle 31. For example, in a state in which the patient assumes a predetermined posture (lithotomy position), the puncture needle 31 can puncture the left and right obturator foramen 400a and 400b of the pelvis in a comparatively perpendicular direction. Therefore, puncture of the puncture needle 31 can be readily carried out. In addition, by puncturing the obturator foramen 400a and 400b in a comparatively perpendicular direction with the puncture needle 31, the puncture needle 31 passes a shallow portion of the tissue, and therefore, the needle tip 315 of the puncture needle 31 can pass from and to the left and right obturator foramen 400a and 400b over a shorter distance. Since the puncture needle 31 can pass rather near to the pubic symphysis of the obturator foramen 400a and 400b, preferably pass a safety zone, the puncture needle 31 can puncture a region, which can include a comparatively small number of nerves and blood vessels to which damage is to be avoided, in safety. Therefore, the invasion can be further reduced and the burden on the patient can be reduced. In this manner, by setting the inclination angle θ so as to be included in the range described above, puncture of the patient by the puncture needle 31 can be carried out appropriately. In contrast, if the inclination angle θ is smaller than the lower limit value or greater than the upper limit value of the range described above, then depending upon the individual difference of the patient or the posture of the patient during manipulation or the like, the puncture needle 31 may not be able to grasp the obturator foramen 400a and 400b widely in plane or the puncture path of the puncture needle 31 may not be reduced in length sufficiently. Therefore, preferably the puncture needle 31 punctures the left and right obturator foramen 400a and 400b of the pelvis in the perpendicular direction.

Further, by the puncture at the angle described above, the tissue between a middle urethra representative of an intermediate region of the urethra 100 in the lengthwise direction and the vagina 200 can easily be targeted. The region between the middle urethra and the vagina 200 is a position suitable as a region into which the implant 8 is to be embedded to carry out treatment of urinary incontinence. In accordance with an exemplary embodiment, More preferably, the region between the middle urethra and the vagina 200 can be easily punctured, if the region is punctured in a state in which the position of the urethra 100 or the vagina 200 or of both of the urethra 100 and the vagina 200 is displaced so as to be pushed to the inner side of the body. Means for pushing one of the urethra 100 and the vagina 200 to the inner side of the body moves the urethral insertion member 800 and the vaginal insertion member 900 to the inner side of the body along the respective axial lines to a predetermined position before puncture, for example, after the urethral insertion member 800 and/or the vaginal insertion member 900 are placed into a state in which they are inserted to an appropriate position. In this case, if a visually observable marker or a marker, which can be imaged on a non-invasive body monitor by X rays or ultrasonic waves is applied to the urethral insertion member 800 and/or the vaginal insertion member 900, then the distance of movement of the member can be recognized.

In accordance with an exemplary embodiment, by causing the puncture needle 31 to perpendicularly puncture the left and right obturator foramen 400a and 400b of the pelvis in a state in which the position of at least one of the urethra 100 and the vagina 200 is displaced so as to be pushed in to the inner side of the body, a path can be formed at a position suitable for indwelling of the implant 8.

In accordance with an exemplary embodiment, preferably, the locus of the puncture needle 31 is set so as to pass a safety zone of the left and right obturator foramen 400a and 400b of the pelvis, and at least one of the urethra 100 and the vagina 200 is displaced to the inner side of the body so that the locus may be positioned between the middle urethra and the vagina 200 thereby to form the path for the puncture needle 31 to puncture along the locus.

Further, at an end portion of the shaft portion 33 on the opposite side to the puncture needle 31, a grip 34 is provided as an operation portion for operating the puncture member 3 to turn. The shape of the grip 34 can be, in the present embodiment, a parallelepiped. When the puncture member 3 is to be turned, the grip 34 is grasped by hand fingers and turned in a predetermined direction. It is to be noted that it is a matter of course that the shape of the grip 34 is not limited to this.

The connection portion 32 is a portion which connects the proximal end of the puncture needle 31 and the shaft portion 33 to each other.

The constituent material of the puncture member 3 is not limited particularly, and, for example, various metal materials such as stainless steel, aluminum or aluminum alloy, titanium or titanium alloy and so forth or various resin materials can be used.

The urethral insertion member 800 can be, in the present embodiment, fixedly mounted on the supporting member 20. It is to be noted that the urethral insertion member 800 may be provided removably on the supporting member 20. The urethral insertion member 800 is in the form of a straight pipe, and an opening at the proximal end of the urethral insertion member 800 is open to a proximal end face of the supporting member 20. Into the urethral insertion member 800, various elongated medical devices, for example, a balloon catheter (not depicted) having an expandable/contractible balloon provided at a distal end portion thereof can be inserted.

In accordance with an exemplary embodiment, a marker (not depicted) is provided on an outer peripheral portion of the urethral insertion member 800. In this case, the marker is disposed so as to be positioned at the urethral orifice when the urethral insertion member 800 is inserted in the urethra 100 and the distal end portion of the urethral insertion member 800 is positioned immediately before the bladder.

The vaginal insertion member 900 can be, in the present embodiment, fixedly mounted on the supporting member 20. It is to be noted that the vaginal insertion member 900 may be provided removably on the supporting member 20. The vaginal insertion member 900 has a form of a straight bar.

Further, a distal end portion of the vaginal insertion member 900 is rounded. Consequently, the vaginal insertion member 900 can be inserted smoothly into the vagina 200.

The supporting member 20 is a member which supports the puncture member 3 for turning motion and supports the urethral insertion member 800 and the vaginal insertion member 900. It is to be noted that, in FIGS. 1 to 4, the supporting member 20 is not depicted.

The supporting member 20 defines the position of the puncture member 3 such that, when the puncture member 3 is turned to puncture the biological tissue 700, the needle tip 315 of the puncture needle 31 passes a region between the urethra 100 (urethral insertion member 800) and the vagina 200 (vaginal insertion member 900). Consequently, a primary threading hole 500 having an arcuate shape is formed between the urethra 100 and the vagina 200 by the puncture needle 31 (refer to FIGS. 2 and 3).

The constituent material of the supporting member 20 is not limited particularly, and various resin materials such as, for example, polyethylene, polypropylene, polycarbonate and acrylonitrile butadiene styrene copolymer (ABS resin) can be used.

Figure 10:
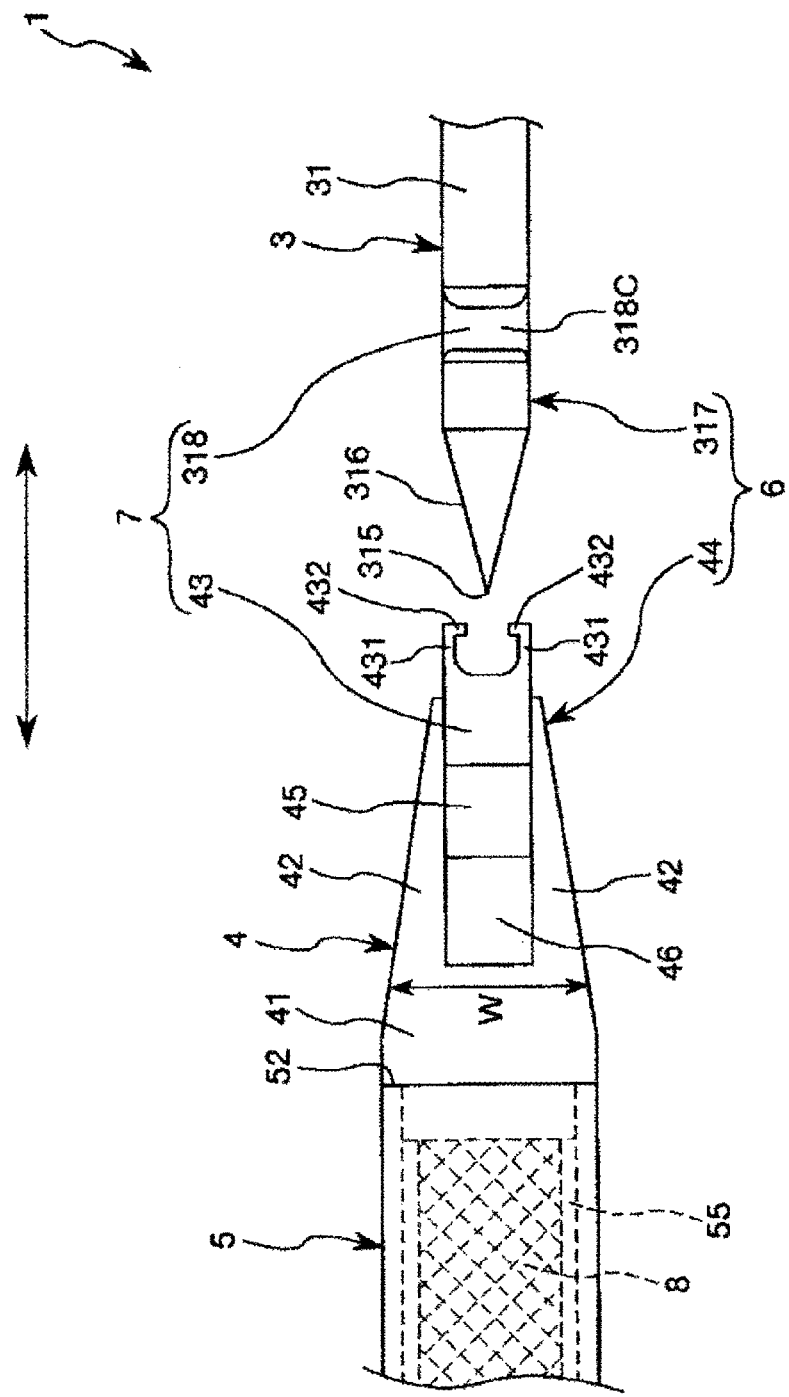
FIG. 10 is a top plan view depicting the medical device according to the first exemplary embodiment of the present disclosure.

As depicted in FIGS. 10 to 12, the connector assembly 2 can include an implant 8 for medical treatment of urinary incontinence to be embedded into a living body, a connector (connector portion) 4 which connects the implant 8 indirectly to a needle tip portion of the puncture needle 31, and a sheath (medical tube) 5.

The connector 4 can include a main body portion 41 in the form of a plate, and a connection portion (second connection portion) 44 having a projection (protrusion portion) 43 which is a connector side projection which projects from the main body portion 41 to the proximal end side in the axial direction. The connector 4 is connected to and used with the puncture needle 31 in a puncture completion state. That means the puncture needle 31 and the connector 4 are connected to each other in a return path.

The main body portion 41 has a flattened shape. The width W of the main body portion 41 is set substantially equal to the width of the implant 8.

The projection 43 has a form of a plate and is disposed so as to extend in parallel to the plane of FIG. 10. Further, the projection 43 has at a proximal end portion thereof a pair of arm portions 431 which are disposed in an opposing relationship to each other, project to the proximal end side and have elasticity. The arm portions 431 are provided in parallel along an upward and downward direction in FIG. 10. Further, pawls 432 are respectively formed at each proximal end portion of the arm portions 431 such that they are disposed in an opposing relationship to each other and project toward the inner side.

In the connection state depicted in FIGS. 11A and 11B in which the puncture needle 31 and the connector 4 are connected to each other, the projection 43 engages with the recessed portion 318 of the connection portion 317 of the puncture needle 31. For example, as the projection 43 and the recessed portion 318 engage with each other, the puncture needle 31 and the connector 4 are connected to each other such that the positional relationship of the puncture needle 31 and the connector 4 in a turning direction around the axis is always fixed, and the connection state is maintained with certainty. In accordance with an exemplary embodiment, for example, inadvertent cancellation of the connection state can be prevented. Consequently, the implant 8 can be embedded such that the direction thereof coincides with a target direction. It is to be noted that the connection mechanism 6 is configured from the connection portion 44 and the connection portion 317. The connection mechanism 6 is configured such that the puncture needle 31 and the connector 4 are connected to each other by moving the puncture needle 31 and the connector 4 relative to each other in the axial direction. Consequently, the connector 4 can turn together with the puncture needle 31.

The projection 43 servers also as a second rotation restriction portion. In the connection state of the puncture needle 31 and the connector 4 depicted in FIGS. 11A and 11B, a lower face (abutting face) 433 and an upper face (abutting face) 434 of the projection 43 abut with an inner face of the recessed portion 318 of the puncture needle 31, for example, with the bottom face 318a and the top face 318b in the recessed portion 318, respectively, whereby the rotation of the connector 4 around the axis with respect to the puncture needle 31 is prevented (restricted). Consequently, the implant 8 can be embedded such that the direction of the implant 8 becomes a target direction. It is to be noted that the rotation restriction mechanism 7 is configured from the projection (second rotation restriction portion) 43 and the recessed portion (first rotation restriction portion) 318.

Further, the main body portion 41 has a taper portion formed thereon such that the width W (length in the upward and downward direction in FIG. 10) thereof gradually increases from the proximal end side to the distal end side (forwardly in the moving direction). The opposite side portions of the main body portion 41 (the opposite end portions in the upward and downward direction in FIG. 10) can include a dissection portion (or separation unit) 42 which dissects (or separates) the biological tissue 700 with a width substantially equal to the width of the implant 8 as the opposite side portions turn to form a secondary threading hole 501 of an arcuate shape.

The main body portion 41 of the connector 4 on which the dissection portion 42 is formed can be connected to the puncture needle 31 (refer to FIGS. 3 and 4). Further, since the connector 4 is, in the connection state, restricted against rotation with respect to the puncture needle 31 by the rotation restriction mechanism 7, in a return path, the direction in which the dissection portion 42 dissects (or separates) the biological tissue 700 is fixed.

In such a return path as just described, the secondary threading hole 501 having a flattened transverse sectional shape can be formed by the dissection portion 42. It is to be noted that the connector 4 is connected such that, when it passes a region between the urethral insertion member 800 and the vaginal insertion member 900, the longitudinal directions of the urethral insertion member 800 and the vaginal insertion member 900 and the widthwise direction of the connector 4 become parallel to each other.

Here, a process in which the secondary threading hole 501 is formed by the dissection portion 42 is described.

First, a primary threading hole 500 having such a circular transverse sectional shape as depicted in FIG. 13A is formed on a forward path. Then, in the puncture completion state depicted in FIG. 2, the connector 4 is connected to the puncture needle 31. While this connection state is kept, in a return path, the proximal end of the main body portion 41 of the connector 4 passes (turns) along the primary threading hole 500 toward this side of the plane of FIG. 13A (refer to FIGS. 3 and 4). Consequently, as depicted in FIG. 13B, the dissection portion 42 dissects the biological tissue 700 so as to tear the same in directions indicated by arrow marks in FIG. 13B from start points of a pair of points S opposing to the primary threading hole 500. For example, the directions in which the dissection portion 42 dissects the biological tissue 700 are parallel to the urethral insertion member 800 and the vaginal insertion member 900.

Further, if the dissection portion 42 passes from the proximal end to the distal end thereof through the primary threading hole 500 as depicted in FIG. 13C, then in the region passed by the dissection portion 42, a secondary threading hole 501 of a width W2 equal to or greater than the width W1 of the primary threading hole 500 and the width W of the connector 4 is formed.

Since the dissection portion 42 dissects the biological tissue 700 in directions parallel to the urethral insertion member 800 and the vaginal insertion member 900, the secondary threading hole 501 has a flattened shape whose longitudinal direction is a parallel direction to the urethral insertion member 800 and the vaginal insertion member 900 (refer to FIGS. 13B and 13C).

Further, as described hereinabove, the maximum value of the width W of the main body portion 41 of the connector 4 is set substantially equal to the width of the implant 8. Consequently, in the return path, the biological tissue 700 can be dissected in just proportion to embed the implant 8 into the living body, and the secondary threading hole 501 having the width W2 necessary and sufficient for the biological tissue 700 can be formed. Therefore, the implant 8 can be embedded with certainty such that direction of the implant 8 becomes a target direction, for example, the upper face of the implant becomes substantially parallel to the urethral insertion member 800 (urethra 100).

Further, on the proximal end side of the main body portion 41, for example, at the distal end side of the projection 43 of the main body portion 41, a hole portion 45 is formed such that, when the puncture needle 31 and the connector 4 are connected to each other, a needle tip portion of the puncture needle 31 is inserted into the hole portion 45. The hole portion 45 has a size with which the needle tip portion of the puncture needle 31 can be inserted and extends through the main body portion 41 in a direction perpendicular to the plane of FIG. 10.

Further, a recessed portion 46 is formed at the distal end side of the hole portion 45 of the main body portion 41 such that it communicates with the hole portion 45. The recessed portion 46 is open to the rear face side of the plane of FIG. 10. When the puncture needle 31 and the connector 4 are connected to each other, the recessed portion 46 can prevent the needle tip 315 of the puncture needle 31 and the main body portion 41 from interfering with each other.

The constituent material of the connector 4 is not limited particularly, and various resin materials such as, for example, polyethylene, polypropylene, polycarbonate and acrylonitrile butadiene styrene copolymer (ABS resin) can be used.

A proximal end portion of the sheath 5 is connected to a distal end portion of the connector 4.

As depicted in FIGS. 3 to 5 and 10, the sheath 5 is a tube (pipe member) which has a distal end opening 51 open at the distal end thereof and a proximal end opening 52 open at the proximal end thereof. The sheath 5 is curved in an arc.

A lumen 55 is formed in the sheath 5 and is open to the distal end opening 51 and the proximal end opening 52. The implant 8 can be inserted into the lumen 55. It is to be noted that, while the formation number of lumens in the present embodiment is one, the formation number is not limited to this and may be, for example, two or more.

Figure 14A:
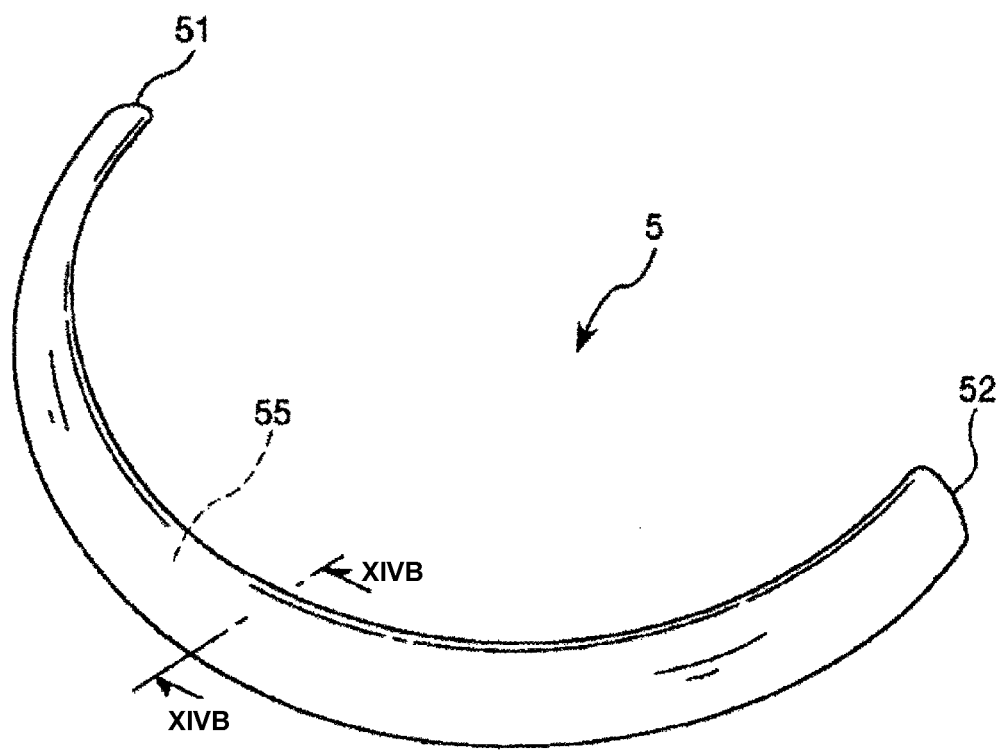
FIG. 14A is a perspective view of a sheath depicted in FIG. 3.
Figure 14B:
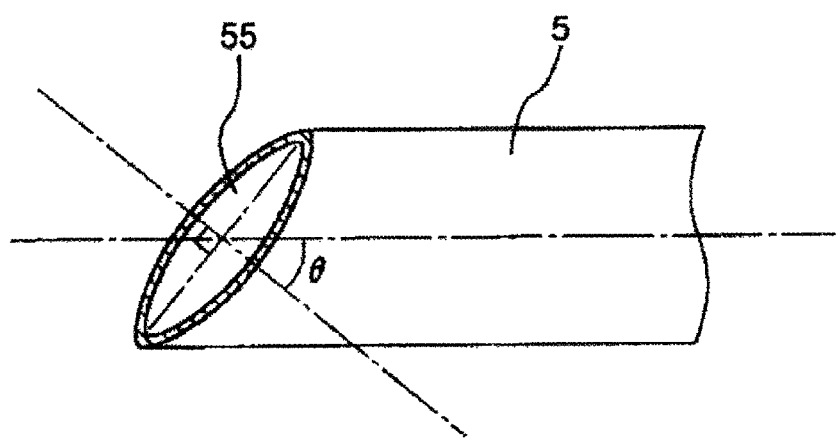
FIG. 14B is a sectional view taken along line XIVB-XIVB of FIG. 14A.

Further, as depicted in FIG. 14A, the sheath 5 has a flattened transverse sectional shape and is curved in an arc over an overall length of the sheath 5 in the longitudinal direction. Further, as depicted in FIG. 14B, the sheath 5 is inclined by an inclination angle θ with respect to the center axis of the curved shape thereof. Consequently, when the sheath 5 in the connection state in which it is connected to the puncture needle 31 through the connector 4 passes between the urethral insertion member 800 and the vaginal insertion member 900 (on the far side of the urethral insertion member 800 or on the near side of the vaginal insertion member 900 with respect to the center axis of turning motion of the puncture needle 31), since it is connected to the puncture needle 31 connected to the shaft portion 33 inclined by the inclination angle θ, the sheath 5 is positioned in parallel to the urethral insertion member 800 and the vaginal insertion member 900. In accordance with an exemplary embodiment, for example, the longitudinal direction of the transverse sectional shape of the sheath 5 is parallel to the urethral insertion member 800 and the vaginal insertion member 900 in the connected state. It is to be noted that the longitudinal direction of the transverse sectional shape of the sheath 5 can coincide with the direction in which the dissection portion 42 dissects the biological tissue 700. Consequently, the sheath 5 is threaded readily into the secondary threading hole 501 formed by dissection of the biological tissue 700 by the dissection portion 42.

Further, the sheath 5 may be of the hard type or may be of the soft type. In accordance with an exemplary embodiment, for example, the sheath 5 may have flexibility. In the present embodiment, the sheath 5 is of the hard type. Here, the term "hard" is used to correspond to such a degree that the sheath 5 can maintain its arcuately curved state. Further, the degree of the curve (curvature) of the sheath 5 preferably is substantially equal to or smaller than the degree of the curve of the puncture needle 31.

Such a configuration as described above can help prevent, when the sheath 5 is inserted into the secondary threading hole 501 formed by the puncture needle 31 and the dissection portion 42 of the connector 4, that the sheath 5 is crushed (compressed) in the secondary threading hole 501, and can cause the sheath 5 to follow (move along) the curved shape of the secondary threading hole 501. Consequently, an operation for inserting the sheath 5 into the secondary threading hole 501 (living body) together with the implant 8 can be readily carried out and with relative certainty. Further, by pulling out the sheath 5 from the secondary threading hole 501 as hereinafter described above after the insertion operation, the implant 8 can be indwelled readily and with certainty into the secondary threading hole 501 (refer to FIG. 6).

As depicted in FIGS. 11A and 11B, the transverse sectional shape of the sheath 5 is a flattened shape, for example, an elliptic shape. Therefore, when the implant 8 of a belt-like shape is inserted into the lumen 55 in advance, the insertion work can be carried out readily. Further, it is possible to form a space through which the implant 8 can be inserted with relative certainty into the secondary threading hole 501. In addition, the direction of the implant 8 can be regulated.

It is to be noted that the transverse sectional shape of the sheath 5 is not limited to a flattened shape but may be some other shape such as, for example, a circular shape.

Further, the thicknesswise direction of the flattened shape of the sheath 5 coincides with the thicknesswise direction of the flattened shape of the main body portion 41 of the connector 4, and the widthwise direction of the flattened shape of the sheath 5 coincides with the widthwise direction of the flattened shape of the main body portion 41 of the connector 4. In this case, preferably an outer circumferential face of the connector 4 and an outer circumferential face of the sheath 5 are continuous to each other.

In accordance with an exemplary embodiment, the sheath 5 preferably has an overall length which is greater than the overall length of the puncture needle 31. Consequently, the sheath 5 is longer than the overall length of the secondary threading hole 501 formed by the puncture needle 31, and in a state in which the sheath 5 is threaded in the secondary threading hole 501, the opposite end portions of the sheath 5 project from the secondary threading hole 501. Then, when the sheath 5 is to be pulled out from the secondary threading hole 501, each of the projecting portions of the sheath 5 can be grasped to perform a pulling out operation of the sheath 5.

The constituent material of the sheath 5 is not limited particularly. For example, polyethylene, polypropylene, polyolefin such as ethylene-vinyl acetate copolymer, modified polyolefin, polyamide (examples: nylon 6, nylon 46, nylon 66, nylon 610, nylon 612, nylon 11, nylon 12, nylon 6-12, and nylon 6-66), thermoplastic polyimide, liquid crystal polymer such as aromatic polyester, polyphenylene oxide, polyphenylene sulfide, polycarbonate, polymethylmethacrylate, polyether, polyether ether ketone, polyetherimide, polyacetal, various thermoplastic elastomers such as styrene-based, polyolefin-based, polyvinyl chloride-based, polyurethane-based, polyester-based, polyamide-based, polybutadiene-based, trans-polyisoprene-based, fluorine-containing rubber-based and chlorinated polyethylene-based elastomers, and copolymers, blends, polymer alloys and so forth which contain any of the materials are available. Mixtures containing one or more of the materials may be used.

Figure 7:
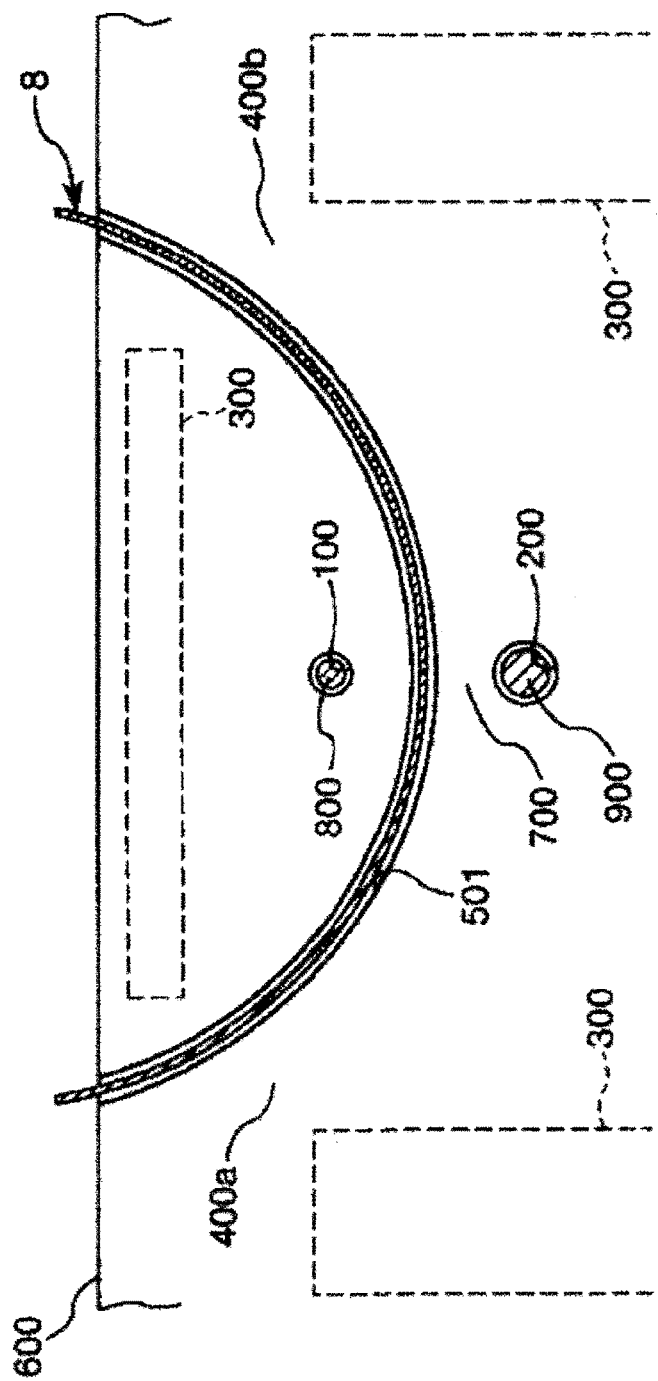
Figure 8:
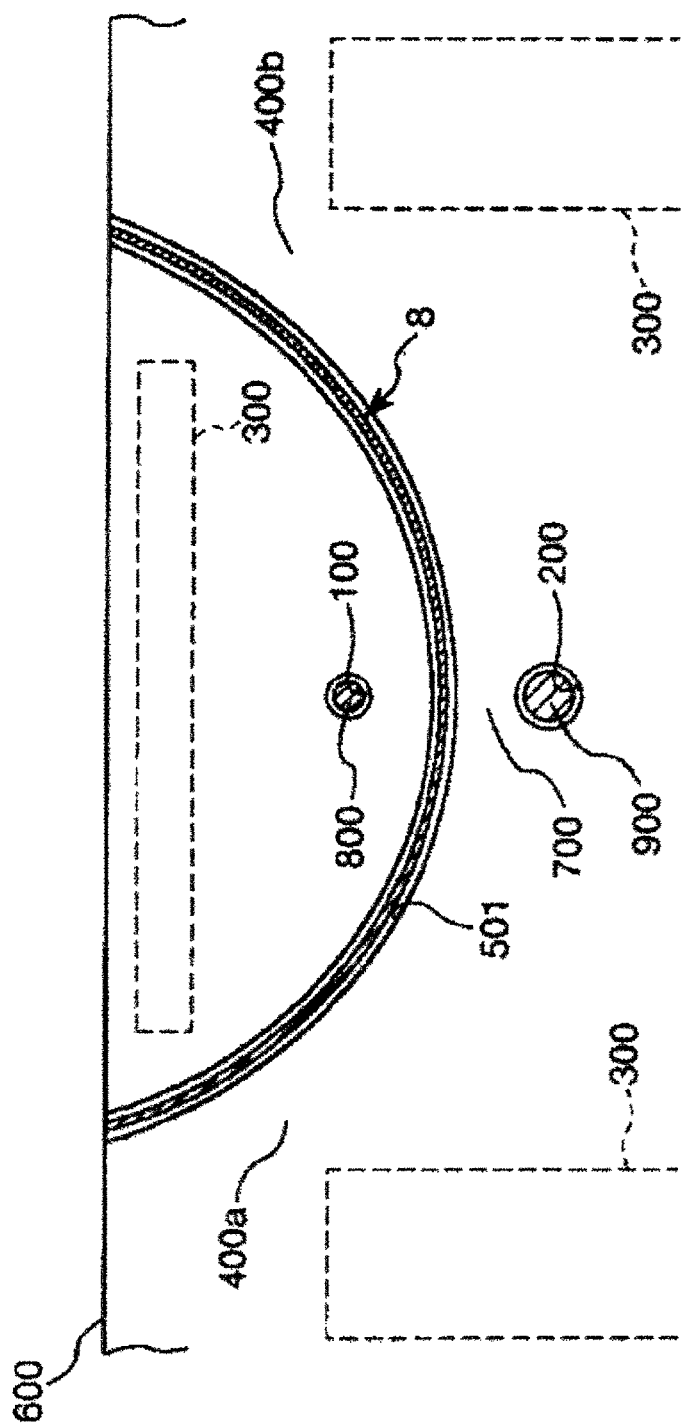

The implant 8 is generally called "sling" and is a device which can be embedded for treatment of urinary incontinence of a female, for example, a device for supporting the urethra 100, for example, a device which supports, for example, when it is tried to move the urethra 100 toward the vagina 200 side, the urethra 100 so as to restrict the movement of the urethra 100 in a direct in which it is spaced away from the vagina 200 (refer to FIG. 8). The implant 8 can be configured from a member having flexibility and having a belt-like (elongated) shape (refer to FIGS. 3 to 8). The implant 8 is accommodated in the sheath 5. Further, the implant 8 may be connected to or not connected to the connector 4. It is to be noted that, in the present embodiment, a proximal end portion of the implant 8 is connected to a distal end portion of the connector 4.

Further, in the present embodiment, the implant 8 has a form of a net. The implant 8 can be configured from an article formed by crossing linear objects with each other into a braid (lattice shape), for example, a net-like braid. The linear objects may be those having a circular transverse sectional shape, or those having a flattened transverse sectional shape, for example, those of strip-like shape (ribbon shape).

It is to be noted that it is a matter of course that the implant 8 is not limited to the net-like article described above.

Further, the constituent material of the implant 8 is not limited particularly, and, for example, various resin materials, fibers or the like having biocompatibility such as polypropylene can be used.

Further, the implant 8 may be inserted (accommodated) in the sheath 5 in advance as depicted in FIG. 3 or may be inserted into the sheath 5 midway of the manipulation. Where the implant 8 is inserted in the sheath 5 in advance, a rapid manipulation can be carried out. Where the implant 8 is inserted into the sheath 5 midway of manipulation, the implant 8 suitable for the case can be selected every time. It is to be noted that, in the description of the present embodiment, a case is described representatively in which the implant 8 is inserted in the sheath 5 in advance.

As depicted in FIGS. 3 and 4, by operating, in the connection state of the puncture needle 31 and the connector 4, the puncture member 3 to turn in the clockwise direction in FIGS. 3 and 4, the biological tissue 700 can be punctured with the puncture needle 31 and the sheath 5 together with the implant 8 can be pulled while the region punctured by the puncture needle 31 of the biological tissue 700 is dissected further by the dissection portion 42 of the connector 4. Consequently, the sheath 5 can be threaded into the secondary threading hole 501 together with the implant 8, and also later indwelling of the implant 8 into the secondary threading hole 501 can be readily carried out.

Now, an example of a manner of use of the medical device 1 is described with reference to FIGS. 1 to 8 and 12A to 12C.

Figure 1:
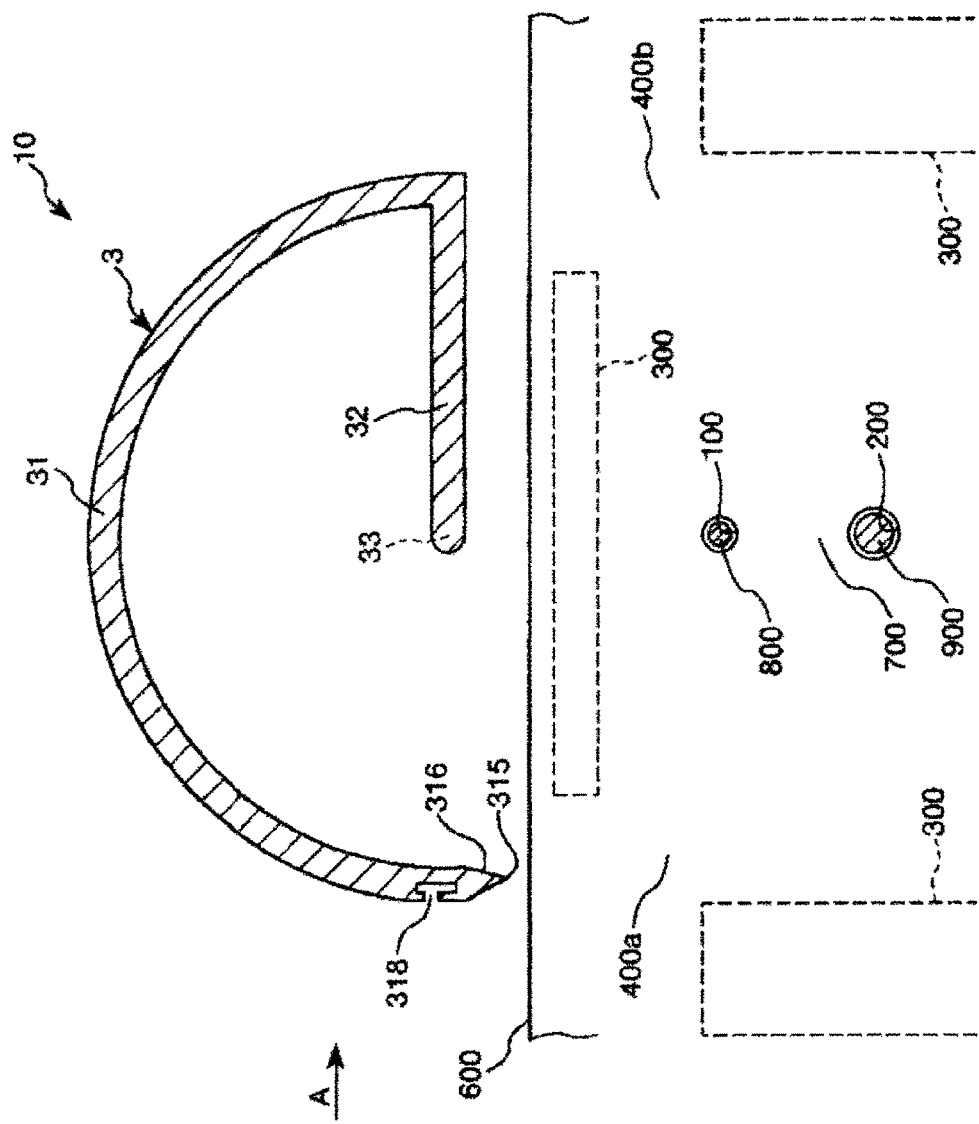
FIGS. 1 to 8 are cross sectional views illustrating successive steps of a process of use of a medical device according to a first exemplary embodiment of the present disclosure.

First, the puncture device 10 is mounted on the living body surface 600 of a patient as depicted in FIG. 1. The mounted position of the puncture device 10 may be a position at which the urethra 100 is supported suitably by an implant 8 to be embedded.

Figure 2:
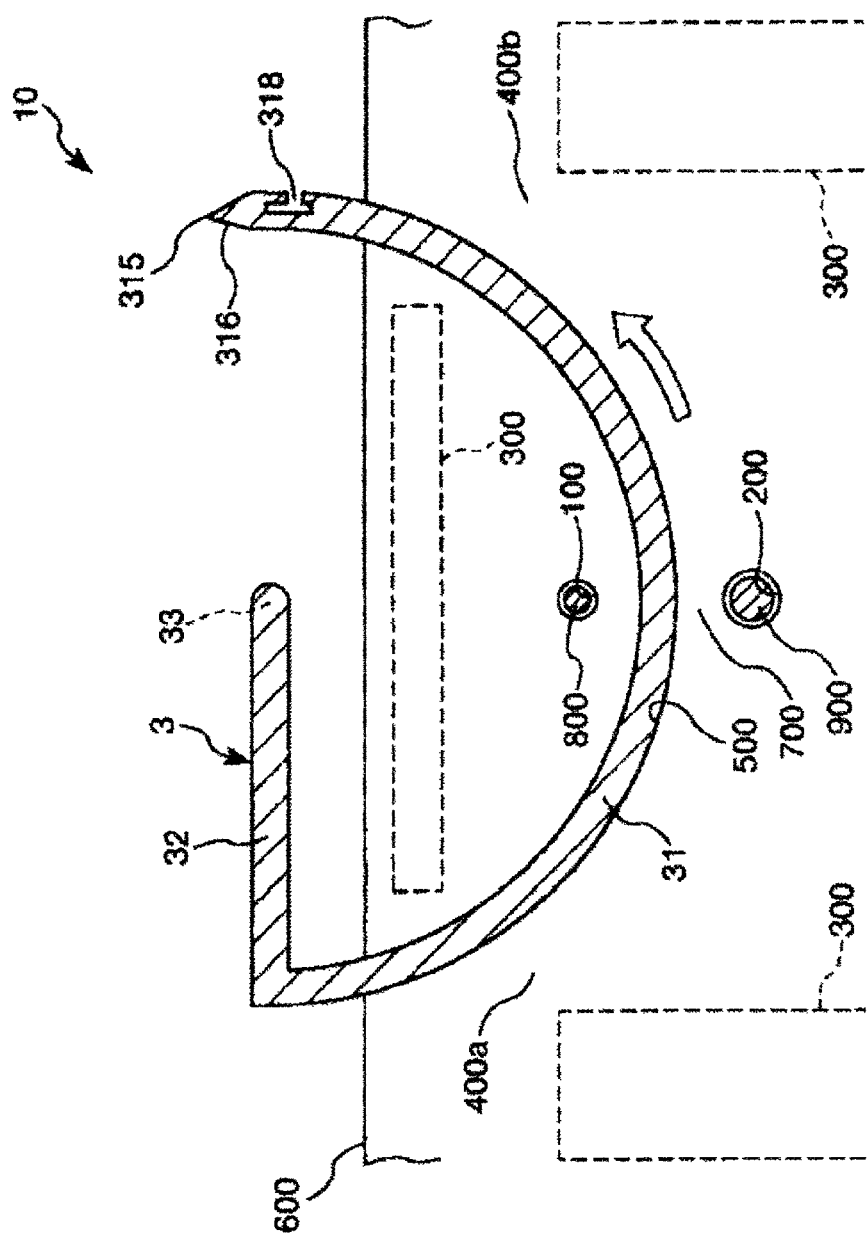

Then, the grip 34 of the puncture device 10 is grasped by one hand and the puncture member 3 is turned in the counterclockwise direction as depicted in FIG. 2 (forward path). Consequently, the puncture needle 31 is turned around the center of turning motion provided by the shaft portion 33 and successively passes the left side inguinal region (or a region in the proximity of the left side inguinal region) of the living body surface 600 of the patient, the obturator foremen 400a of the pelvis 300, the region between the urethra 100 and the vagina 200, the obturator foremen 400b of the pelvis 300 and the right side inguinal region (or a region in the proximity of the right side inguinal region) of the living body surface 600, for example, successively punctures the portions mentioned. By this puncture, a primary threading hole 500 is formed in the biological tissue 700 such that it extends from the left side inguinal region to the right side inguinal region of the living body surface 600. Further, the puncture needle 31 projects at the connection portion 317 thereof from the right side inguinal region of the living body surface 600.

Then, a connector assembly 2 is prepared. Then, the connector 4 and the puncture needle 31 are connected to each other by the connection mechanism 6 as depicted in FIG. 3.

Figure 12A:
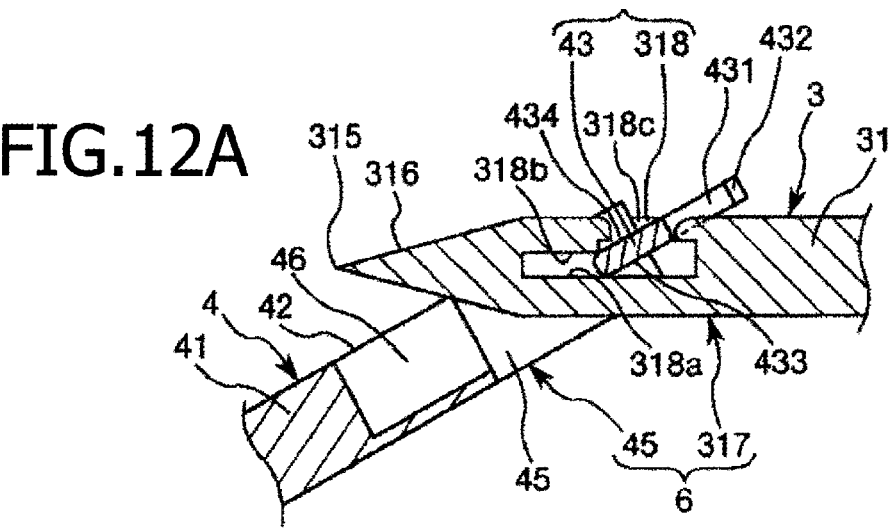
FIGS. 12A, 12B, and 12C are cross sectional views illustrating a procedure of connecting the puncture needle and the connector of the medical device depicted in FIG. 10.

Thereupon, the needle tip portion of the puncture needle 31 is inserted into the hole portion 45 from the lower side of the hole portion 45 of the connector 4 in FIG. 12A as depicted in FIG. 12A. In this case, the entrance 318c of the recessed portion 318 of the puncture needle 31 is directed to the upper side in FIG. 12A. Further, a portion of the projection 43 of the connector 4 on the distal end side is inserted into the recessed portion 318 of the puncture needle 31.

Figure 12B:
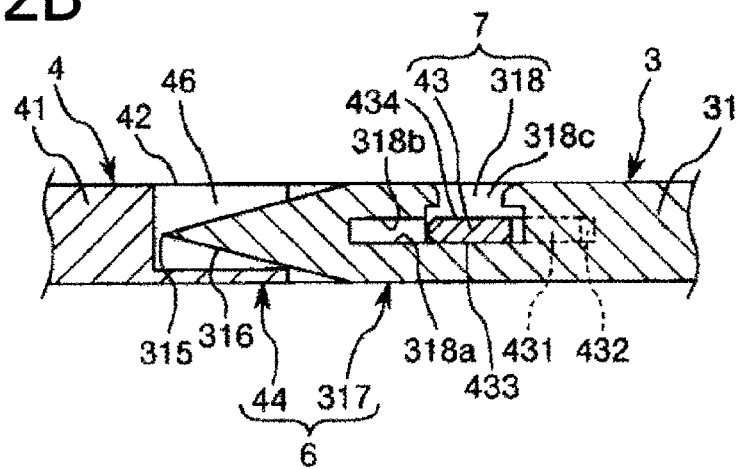
Figure 12C:
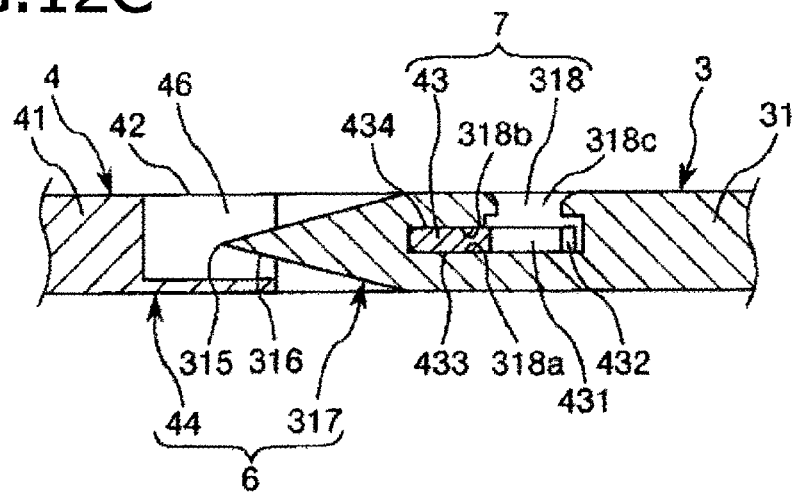

Then, as depicted in FIG. 12B, the connector assembly 2 is moved in a direction toward the distal end with respect to the puncture needle 31 and is rotated by a predetermined angle in the clockwise direction in FIG. 12B. Then, the connector assembly 2 is moved further in the direction toward the distal end with respect to the puncture needle 31 as depicted in FIG. 12C. Thereupon, the arm portions 431 of the projection 43 of the connector 4 are curved and spread in directions in which they are spaced apart from each other. Thereafter, the arm portions 431 are inserted into the recessed portion 318 and restore their original shape assumed in the natural state.

Consequently, the projection 43 and the recessed portion 318 are engaged with each other to connect the puncture needle 31 and the connector 4 to each other. Thereafter, the connection state between the puncture needle 31 and the connector 4 is maintained. Further, the puncture needle 31 and the connector 4 are connected to each other such that the positional relationship of the puncture needle 31 and the connector 4 in the rotational direction around the axis may always be fixed.

Further, in the connection state of the puncture needle 31 and the connector 4 depicted in FIG. 12C, the lower face 433 and the upper face 434 of the projection 43 abut with the bottom face 318a and the top face 318b in the recessed portion 318 of the puncture needle 31, respectively. Consequently, rotation of the connector 4 around the axis with respect to the puncture needle 31 is blocked. Further, since the pawls 432 of the arm portions 431 or the projection 43 are abutted with the proximal end side of the top face 318b in the recessed portion 318, unnecessary cancellation of the connection state of the puncture needle 31 and the connector 4 can be prevented.

Further, as described hereinabove, in the operation for connecting the puncture needle 31 and the connector 4 to each other, the puncture needle 31 and the connector 4 are connected to each other by finally moving the connector assembly 2 in the direction toward the distal end with respect to the puncture needle 31. Therefore, it can be prevented that the puncture needle 31 projecting to the outside from the living body surface 600 enters the living body.

Then, the grip 34 of the puncture device 10 is grasped by one hand to turn the puncture member 3 in the opposite direction, for example, in the clockwise direction in FIG. 4 as depicted in FIG. 4. Consequently, the puncture needle 31 is pulled out from the living body and the dissection portion 42 of the connector 4 is turned together with the puncture needle 31 and threaded into the primary threading hole 500. By the threading, the primary threading hole 500 is expanded in width to form a secondary threading hole 501 (refer to FIG. 13C). While the dissection portion 42 rotates, for example, in the return path, by the rotation restriction mechanism 7, the direction in which the dissection portion 42 dissects the biological tissue 700 is fixed with respect to the urethral insertion member 800 and the vaginal insertion member 900 and besides is a direction parallel to the longitudinal direction of the urethral insertion member 800 and the vaginal insertion member 900. Consequently, the secondary threading hole 501 has a cross sectional shape which is a flattened shape whose longitudinal direction is a direction parallel to the longitudinal direction of the urethral insertion member 800 and the vaginal insertion member 900 over the overall length in the longitudinal direction of the secondary threading hole 501.

Figure 5:
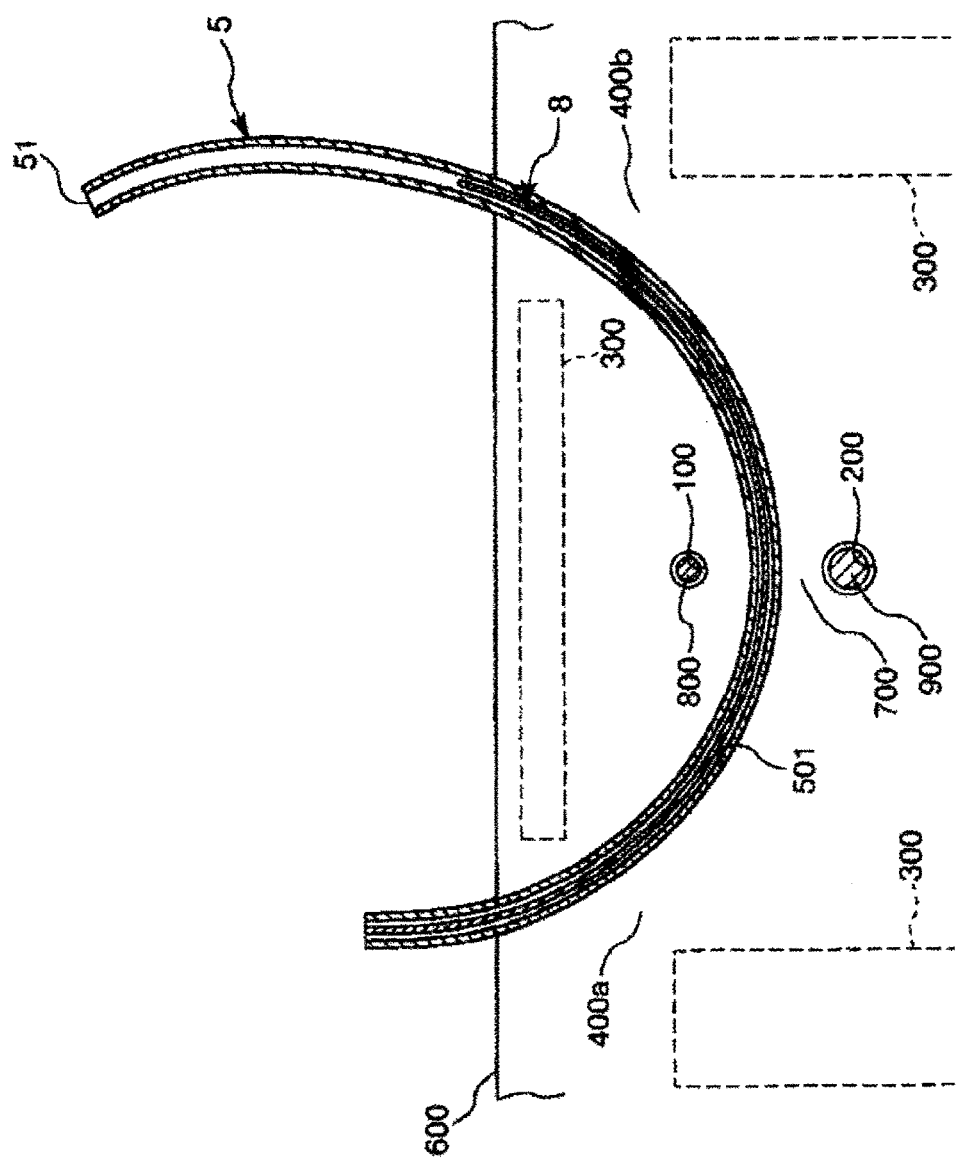
Figure 6:
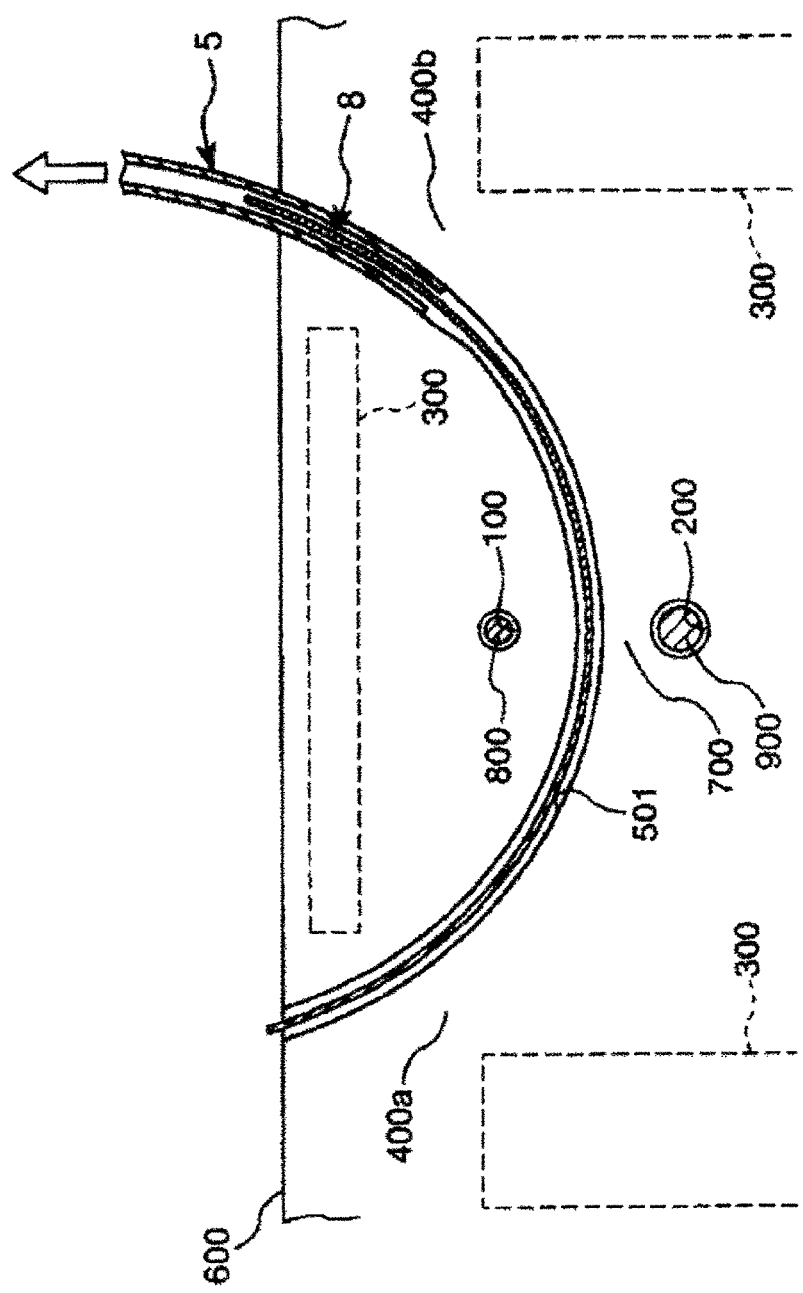

Further, at this time, the connector assembly 2 projects at a region thereof on the distal end side of the sheath 5 from the obturator foramen 400b side of the living body surface 600 and projects at a region on the proximal end side of the connector 4 and the sheath 5 from the obturator foremen 400a side of the living body surface 600 (refer to FIG. 5).

Then, as depicted in FIG. 5, a portion of the sheath 5 on the proximal end side of the sheath 5 and a portion on the proximal end side of the implant 8 are cut, and the puncture member 3 of the puncture device 10 is removed together with the supporting member 20 from the living body surface 600. Thereupon, the connector 4 is removed together with the puncture member 3.

Then, a portion of the sheath 5 projecting from the obturator foremen 400b side of the living body surface 600 is grasped by one hand while a portion of the implant 8 projecting from the obturator foremen 400a side of the living body surface 600 is grasped by the other hand. Then, the sheath 5 is pulled in a direction toward the proximal end to pull out the sheath 5 from the secondary threading hole 501. Consequently, the implant 8 remains threaded in the secondary threading hole 501 as depicted in FIG. 7. This implant 8 assumes a state in which it projects at a portion on the distal end side thereof from the obturator foremen 400b side of the living body surface 600 and projects at a portion on the proximal end side thereof from the obturator foremen 400a of the living body surface 600. Then, a portion of the implant 8 on the distal end side and a portion on the proximal end side of the implant 8 are pulled by predetermined force to adjust the position of the implant 8 with respect to the urethra 100. It is to be noted that, thereupon, tensile force may be exerted in the implant 8. By this, the urethra 100 is pulled in a direction in which it is spaced away from the vagina 200 and is supported from the lower side by the implant 8. Further, as described hereinabove, the secondary threading hole 501 has a transverse sectional shape of a flattened shape whose longitudinal direction is a direction parallel to the longitudinal direction of the urethral insertion member 800 and the vaginal insertion member 900 over the overall length of the secondary threading hole 501 in the longitudinal direction. The implant 8 inserted in such a secondary threading hole 501 as described above has a widthwise direction substantially parallel to the longitudinal direction of the urethra 100 and the vagina 200. Consequently, the upper face of the implant 8 is placed into an opposing state to the urethra 100. As a result, the implant 8 can support the urethra 100 stably.

Then, as depicted in FIG. 8, unnecessary portions of the implant 8 are cut away, and predetermined wound closure or the like is carried out, thereby ending the manipulation.

As described above, with the medical device 1 of the present embodiment, when the implant 8 is to be embed in a predetermined direction into a living body, such embedding can be carried out only by a manipulation of low invasion such as puncture of the biological tissue 700 by the puncture needle 31 and dissecting of the biological tissue 700 by the dissection portion 42, and incision or the like of the vaginal wall whose invasion is high need not be carried out. Therefore, the burden on the patient is relatively light and the safety of the patient is relatively high. Further, such a situation that the implant 8 is exposed to the inside of the vagina through a wound caused by incision as in the case in which the vaginal wall is incised or that such complications as infection from the wound or the like are caused can be prevented, and the implant 8 can be embedded safely.

Further, when the implant 8 is to be embedded, the biological tissue is punctured by the puncture needle 31 and the biological tissue 700 is dissected by the dissection portion 42 to form the secondary threading hole 501. Therefore, the operation for embedding the implant 8 can be readily carried out and with relative certainty.

Furthermore, since the biological tissue can be dissected with a width substantially equal to the width of the implant 8 by the dissection portion 42, the implant 8 can be embedded with relative certainty by a manipulation of very low invasion.

Further, the direction in which the dissection portion 42 dissects the biological tissue 700 is fixed (parallel) with respect to the urethral insertion member 800 and the vaginal insertion member 900 by the rotation restriction mechanism 7. Consequently, the implant 8 can be embedded such that the direction thereof coincides with a target direction (parallel to the urethral insertion member 800 and the vaginal insertion member 900).

Further, since the operator need not carry out incision, damage to the fingertip of the operator can be prevented from a knife or the like.

Figure 15:
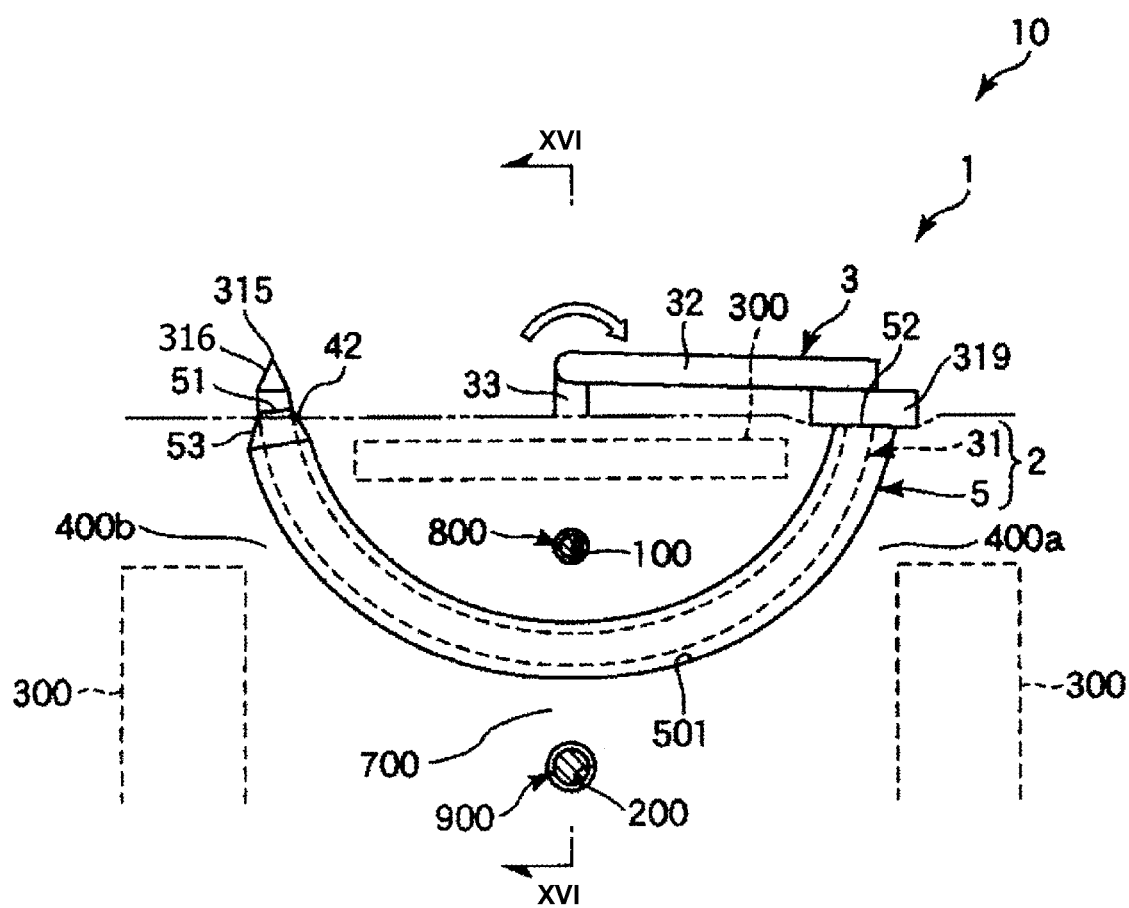
FIG. 15 is a front elevational view depicting a medical device according to a second exemplary embodiment of the present disclosure.
Figure 16:
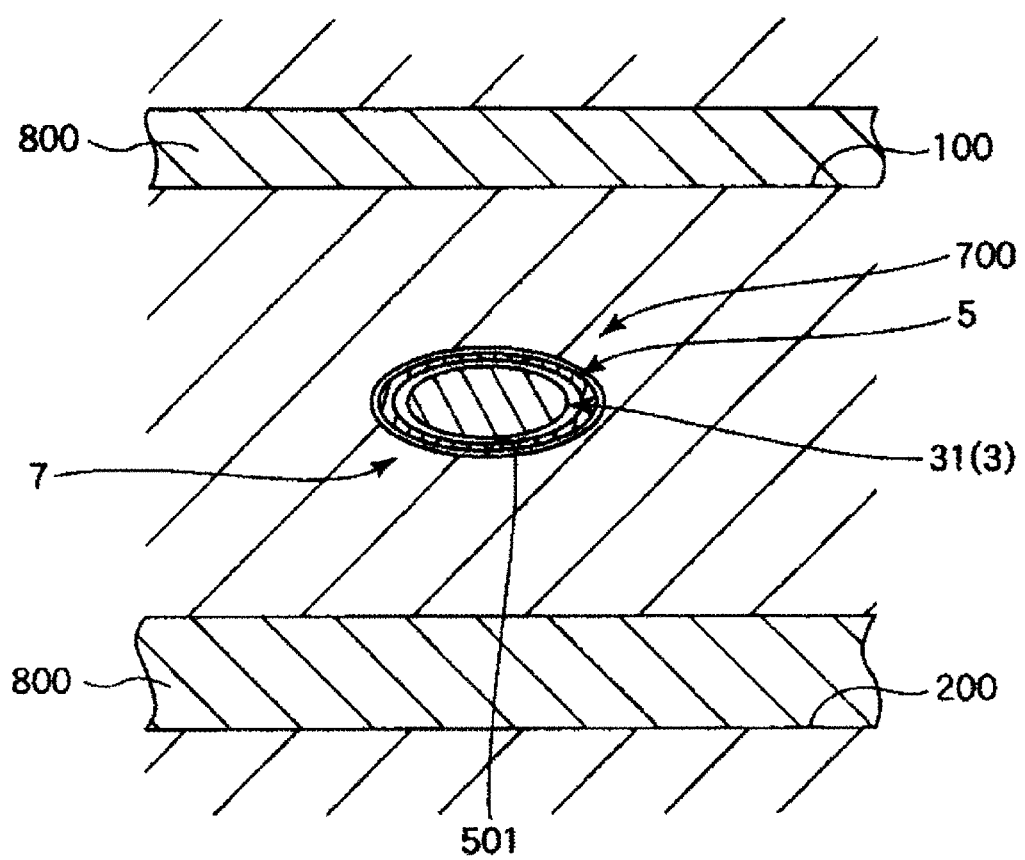
FIG. 16 is a cross sectional view taken along line XVI-XVI of FIG. 15.

FIG. 15 is a front elevational view depicting a medical device according to a second embodiment of the present disclosure, and FIG. 16 is a cross sectional view taken along line XVI-XVI of FIG. 15.

In the following, the medical device according to the second embodiment of the present disclosure is described with reference to FIGS. 15 and 16. However, the description is given principally of differences of the second embodiment from the embodiment described above and description of like matters is omitted herein to avoid redundancy.

The medical device of the present embodiment is similar to that of the first embodiment except that it is different in configuration (shape) of the sheath. It is to be noted that the needle tip 315 of the puncture needle 31 of the present embodiment is directed in a clockwise direction in FIGS. 15 and 16.

As depicted in FIGS. 15 and 16, the sheath 5 and the puncture needle 31 in the present embodiment have a flattened transverse sectional shape (flattened portion).

It is to be noted that, while the flattened shape in the present embodiment is an elliptical shape, the flattened shape is not limited to this, but may be, for example, a diamond shape rounded at the corners thereof, a rectangular shape (flat shape) rounded at the corners thereof, or a spindle shape having an increased width (increased diameter) at a central portion with respect to the opposite end portions thereof.

The sheath 5 and the puncture needle 31 are inserted into the biological tissue 700 in an assembled state in which the puncture needle 31 is inserted in the hollow portion of and assembled to the sheath 5. In this assembled state, the needle tip 315 provided at a distal end portion of the puncture needle 31 projects from the distal end opening 51 of the sheath 5. Consequently, the needle tip 315 can puncture the biological tissue 700.

Further, a tapering portion 316 is provided at a distal end portion of the puncture needle 31 such that the outer diameter thereof gradually increases in a direction from the needle tip 315 toward the proximal end, for example, the tapering portion 316 has a tapering shape. The tapering portion 316 functions as a dissection portion for dissecting the punctured portion of the living body so as to gradually expand the punctured portion as the needle tip 315 punctures the living body. Further, since the transverse sectional shape of the puncture needle 31 is a flattened shape, the transverse sectional shape of the tapering portion 316 is naturally is a flattened shape, and the maximum width of the transverse sectional shape of the tapering portion 316 is substantially equal to the width of the implant 8, and when the primary threading hole 500 is to be formed, the width of the primary threading hole 500 can be made substantially equal to the width of the implant 8. In accordance with an exemplary embodiment, the implant 8 threaded in the primary threading hole 500 can be prevented from contracting in the primary threading hole 500 and can exhibit a sufficiently developed state.

A tapering portion 53 is provided at a distal end portion of the sheath 5 such that the outer diameter thereof from the distal end opening 51 gradually increases in a direction toward the proximal end, for example, the tapering portion 53 has a tapering shape. The tapering portion 53 can function as a dissecting portion for dissecting the living body such that the living body is gradually expanded following the tapering portion 316 of the puncture needle 31 as the needle tip 315 of the puncture needle 31 punctures the biological tissue 700.

In accordance an with an exemplary embodiment, the transverse sectional shape of the sheath 5 is a flattened shape, the transverse sectional shape of the tapering portion 53 is naturally a flattened shape, and the maximum width of the tapering portion 53 is substantially equal to the width of the implant 8 (a little greater than the maximum width of the tapering portion 316). By such a tapering portion 53 as just described, the expanded state of the primary threading hole 500 dissected and expanded by the tapering portion 316 of the puncture needle 31 can be maintained with relative certainty. In accordance with an exemplary embodiment, for example, the secondary threading hole 501 can be formed such that it is expanded to a width substantially equal to the width of the implant 8 or to a width a little greater than the width of the implant 8.

Further, in the assembled state, the puncture needle 31 having a flattened transverse sectional shape and the sheath 5 having a flattened transverse sectional shape overlap with each other. Consequently, the sheath 5 is blocked against rotation around the axis with respect to the puncture needle 31. Further, in the assembled state, the puncture needle 31 curved in an arc and the sheath 5 curved in an arc overlap with each other. Also by the overlap, the sheath 5 is blocked against rotation around the axial line with respect to the puncture needle 31. By such blocking of rotation, the dissecting direction by the tapering portion 316 of the puncture needle 31 and the dissecting direction (expansion direction) by the tapering portion 53 of the tapering portion 53 of the sheath 5 can be maintained such that they become the same direction (fixed direction with respect to the urethral insertion portion 800 and the vaginal insertion member 900) with certainty. In accordance with an exemplary embodiment, for example, the function of the rotation restriction mechanism 7 is exhibited by such overlaps as described above.

Furthermore, an increased diameter portion 319 having an increased outer diameter is provided at a proximal end portion of the puncture needle 31, for example, at a boundary portion of the puncture needle 31 with the connection portion 32 as depicted in FIG. 15. The increased diameter portion 319 abuts with the proximal end of the sheath 5 in the assembled state. Consequently, inadvertent movement of the sheath 5 can be restricted.

Figure 17:
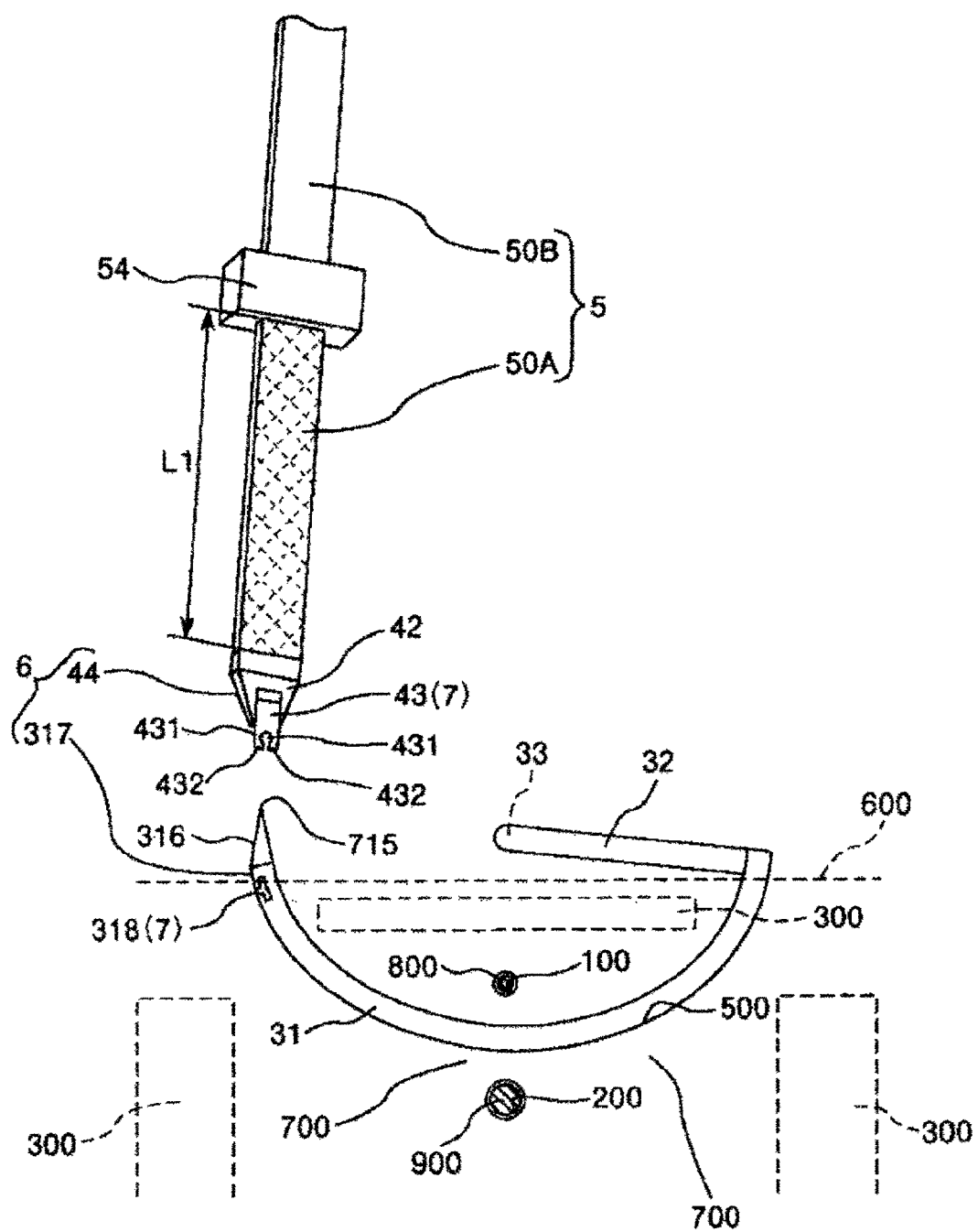
FIGS. 17 to 19 are views illustrating different steps of a process of use of a medical device according to a third exemplary embodiment of the present disclosure.
Figure 18:
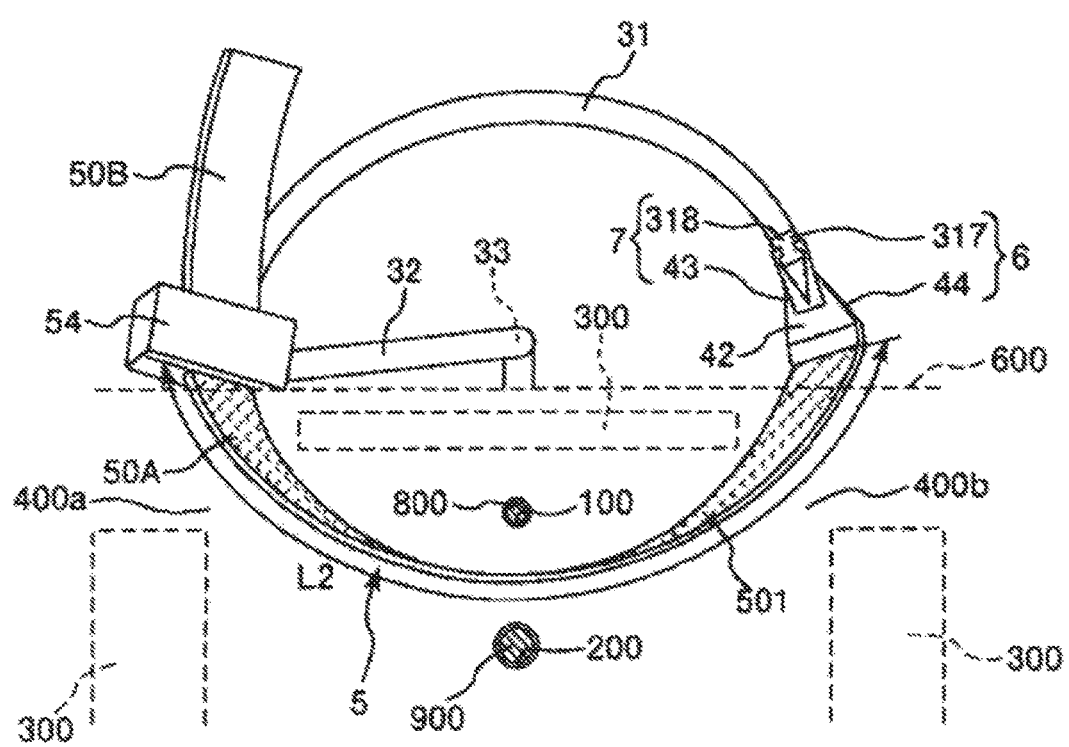
Figure 19:
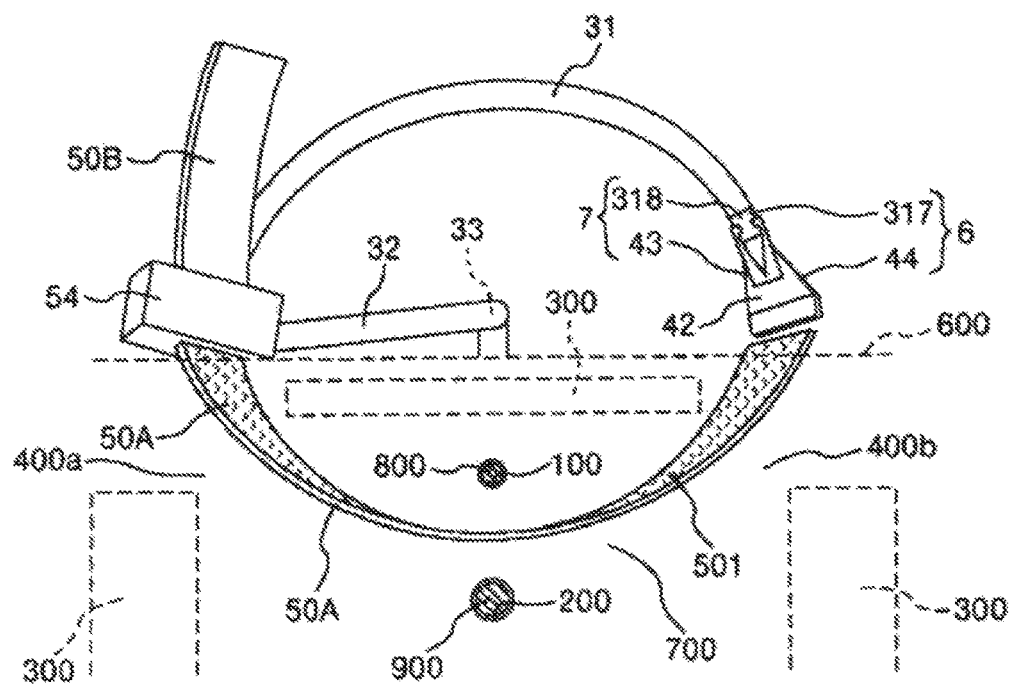

FIGS. 17 to 19 are views illustrating different steps of a process of use of a medical device according to a third embodiment of the present disclosure.

In the following, the medical device according to the third exemplary embodiment of the present disclosure is described with reference to FIGS. 17 and 19. However, the description is given principally of differences of the present embodiment from the embodiments described above and description of like matters is omitted herein to avoid redundancy.

The medical device of the present embodiment is similar to that of the first exemplary embodiment except that it is different principally in configuration (shape) of the medical tube.

As depicted in FIGS. 17 to 19, the sheath 5 in the present embodiment is configured from an inner tube 50A and an outer tube 50B inserted in the inner tube 50A. The inner tube 50A and the outer tube 50B configure a dual pipe structure in which they can move relative to each other. Consequently, the sheath 5 is configured variable in response to the length of the primary threading hole 500.

Further, a flange portion 54 is formed at a distal end portion of the outer tube 50B such that it has an increased diameter. The flange portion 54 functions as a stopper which is abutted with the living body surface 600 to define the movement limit of the outer tube 50B. Consequently, the outer tube 50B is inhibited from being inserted into the living body together with the inner tube 50A.

In an initial state in which the inner tube 50A is not inserted in the living body as depicted in FIG. 17, the length by which the inner tube 50A projects from the outer tube 50B is L1. Thus, if the puncture needle 31 is connected from this initial state to and reversed together with the inner tube 50A, then the flange portion 54 is abutted with the living body surface 600. If the puncture needle 31 is reversed further, then the inner tube 50A moves relative to the outer tube 50B, and the length by which the inner tube 50A projects from the outer tube 50B becomes L2 which is longer than L1 (refer to FIG. 18). Consequently, when embedding of the inner tube 50A into the living body is completed, the proximal end portion of the inner tube 50A can be prevented from entering the living body.

When the inner tube 50A is to be pulled out from within the living body, by cutting a distal end portion of the inner tube 50A as depicted in FIG. 19, the inner tube 50A can be pulled out toward the proximal end side. Consequently, the implant 8 can be indwelled comparatively readily in the living body. It is to be noted that, at this time, the connection mechanism 6 may be canceled to pull out the inner tube 50A in the opposite direction.

Figure 20:
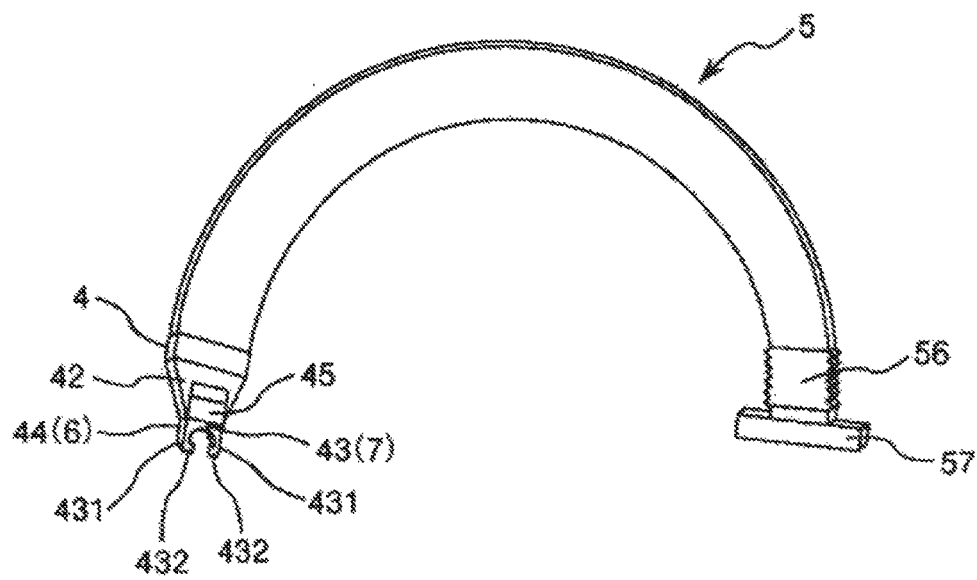
FIG. 20 is a side elevational view depicting a medical tube provided in a medical device according to a fourth exemplary embodiment of the present disclosure.

FIG. 20 is a side elevational view depicting a medical tube provided in a medical device according to a fourth embodiment of the present disclosure.

In the following, the medical device according to the fourth exemplary embodiment of the present disclosure is described with reference to FIG. 20. However, the description is given principally of differences of the present embodiment from the embodiments described hereinabove and description of like matters is omitted herein to avoid redundancy.

The medical device of the present embodiment is similar to that of the third exemplary embodiment described hereinabove except that it is different in form of elongation/contraction of the medical tube.

As depicted in FIG. 20, a flexible portion 56 is provided at a proximal end portion of the sheath 5 in the present embodiment such that it is expandable and contractible in a longitudinal direction thereof. The flexible portion 56 has an accordion shape, which means that the flexible portion 56 has wide portions and narrow portions alternatively disposed in the longitudinal direction of the sheath 5.

Further, a stopper 57 is provided at the proximal end of the sheath 5 by expanding the outer diameter of the sheath 5.

When the sheath 5 is inserted into the living body, the stopper 57 is abutted with the living body surface 600 to restrict the sheath 5 so that a distal end portion of the sheath 5 may not enter the living body surface 600. If the sheath 5 is further moved to the proximal end side, then the flexible portion 56 can be extended in its longitudinal direction. Consequently, the overall length of the sheath 5 increases, and the distal end portion of the sheath 5 can be exposed to the outer side from the living body surface 600 with certainty.

Figure 21:
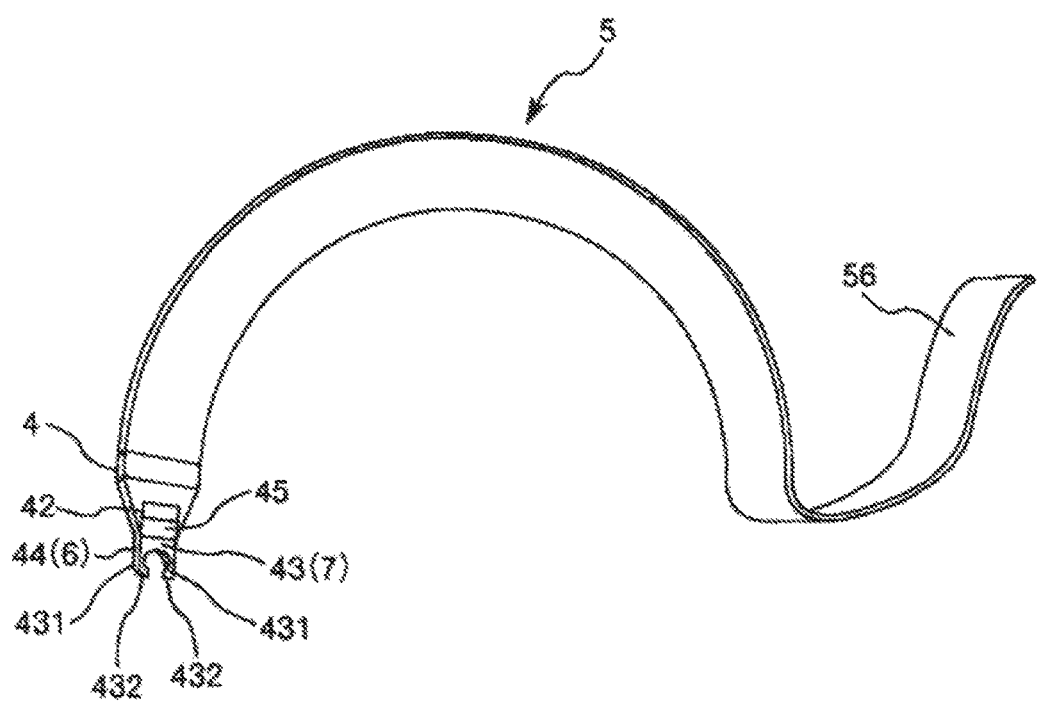
FIG. 21 is a side elevational view depicting a medical tube provided in a medical device according to a fifth exemplary embodiment of the present disclosure.

FIG. 21 is a side elevational view depicting a medical tube provided in a medical device according to a fifth exemplary embodiment of the present disclosure.

In the following, the medical device according to the fifth exemplary embodiment of the present disclosure is described with reference to FIG. 21. However, the description is given principally of differences of the fifth exemplary embodiment from the embodiments described hereinabove and description of like matters is omitted herein to avoid redundancy.

The medical device of the present embodiment is similar to that of the fourth exemplary embodiment described hereinabove except that it is different in configuration (shape) of the flexible portion.

As depicted in FIG. 21, the flexible portion 56 in the present embodiment is configured from an elastic body having elasticity. Consequently, the overall length of the sheath 5 is variable. Therefore, in a state in which the sheath 5 is indwelled in the living body, the distal end portion of the sheath 5 can be exposed to the outer side from the living body surface 600 with certainty.

As the material for configuring the elastic body, for example, various rubber materials such as natural rubber, isoprene rubber, butadiene rubber (polybutadiene), chloroprene rubber, silicone rubber, urethane rubber (polyurethane), fluorine-containing rubber and styrene-butadiene rubber and various thermoplastic elastomers such as styrene-based, polyolefin-based, polyurethane-based, polyester-based, polyamide-based, polybutadiene-based, trans-polyisoprene-based, fluorine-containing rubber-based, and chlorinated polyethylene-based elastomers are available.

Figure 22:
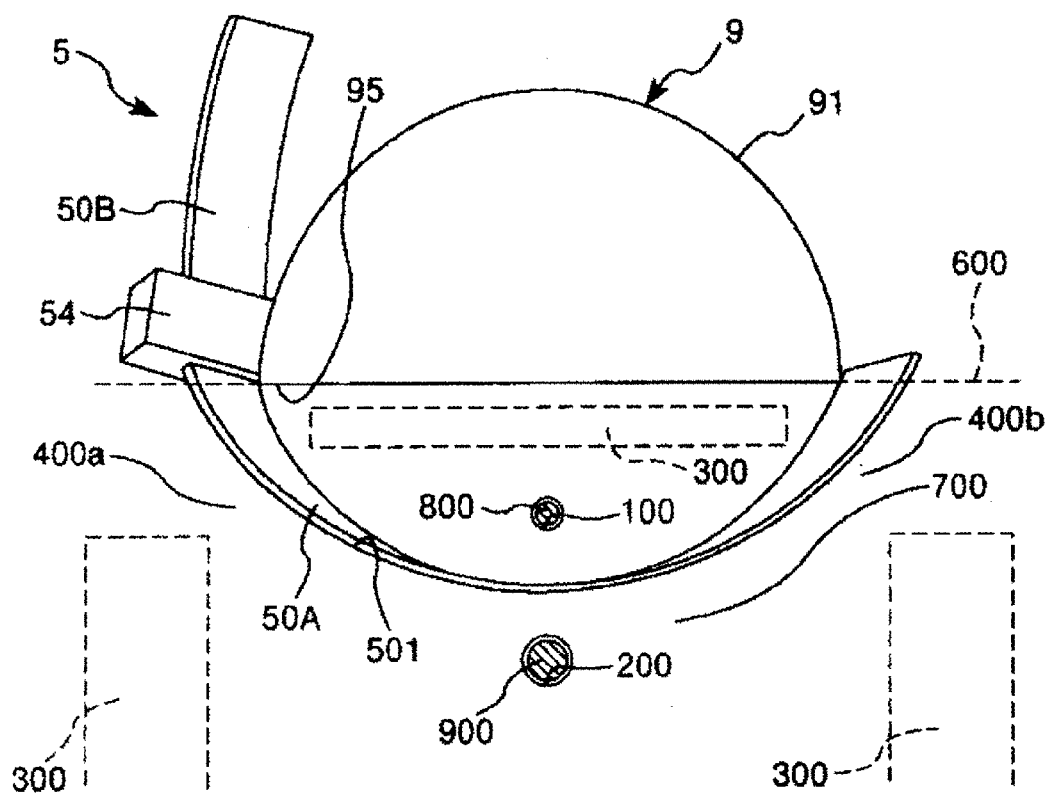
FIG. 22 is a view illustrating a manner of use of a medical device according to a sixth exemplary embodiment of the present disclosure.

FIG. 22 is a view illustrating a manner of use of a medical device according to a sixth exemplary embodiment of the present disclosure.

In the following, the medical device according to the sixth exemplary embodiment of the present disclosure is described with reference to FIG. 22. However, the description is given principally of differences of the sixth exemplary embodiment from the embodiments described hereinabove and description of like matters is omitted herein to avoid redundancy.

The medical device of the present embodiment is similar to that of the first exemplary embodiment described hereinabove except that it is different in the configuration (shape) of the guide member.

As depicted in FIG. 22, the medical device 1 of the present embodiment can include a guide member 9 for guiding the sheath 5 when the sheath 5 is pulled out from the biological tissue 700. The guide member 9 is used in an abutting state in which it abuts with the living body surface 600 when the sheath 5 (inner tube 50A) is to be pulled out.

The guide member 9 is configured from a plate member of a semicircular shape. The guide member 9 has a curved face 91 curved in the same direction as that of the puncture needle 31, and a side face 95 serving as an abutting face which abuts with the living body surface 600.

When the inner tube 50A is to be pulled out from the living body, a distal end portion of the inner tube 50A is grasped and the inner tube 50A is pulled out along the curved face 91. Consequently, the sheath 5 can be pulled out readily by an easy operation of removing the sheath 5 along the curved face of the guide member 9. Particularly where the sheath 5 has flexibility, the burden on the biological tissue 700 can be reduced by the guide member 9. Further, also the outer tube 50B can be pulled out along the curved face 91 similarly.

Figure 23:
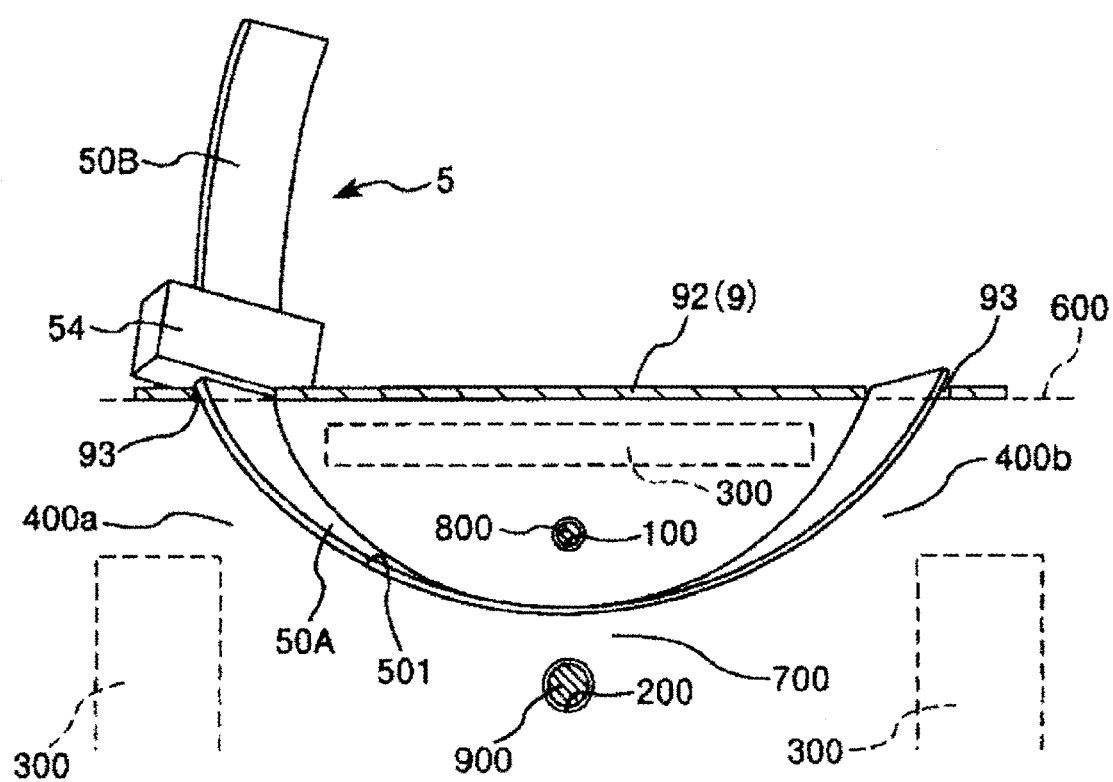
FIG. 23 is a view illustrating a manner of use of a medical device according to a seventh exemplary embodiment of the present disclosure.

FIG. 23 is a view illustrating a manner of use of a medical device according to a seventh exemplary embodiment of the present disclosure.

In the following, the medical device according to the seventh exemplary embodiment of the present disclosure is described with reference to FIG. 23. However, the description is given principally of differences of the seventh exemplary embodiment from the embodiments described hereinabove and description of like matters is omitted herein to avoid redundancy.

The medical device of the present embodiment is similar to that of the first exemplary embodiment described hereinabove except that it is different in configuration (shape) of the guide member.

The guide member 9 in the present embodiment is configured from a plate member 92 having two through-holes 93 into which the opposite end portions of the inner tube 50A are to be inserted.

When the inner tube 50A is to be pulled out, it can be pulled out while an outer peripheral portion of the inner tube 50A is abutted with an edge portion of the right side through-hole 93 in FIG. 23. Consequently, the sheath 5 can be pulled out comparatively readily from the biological tissue 700.

Figure 24:
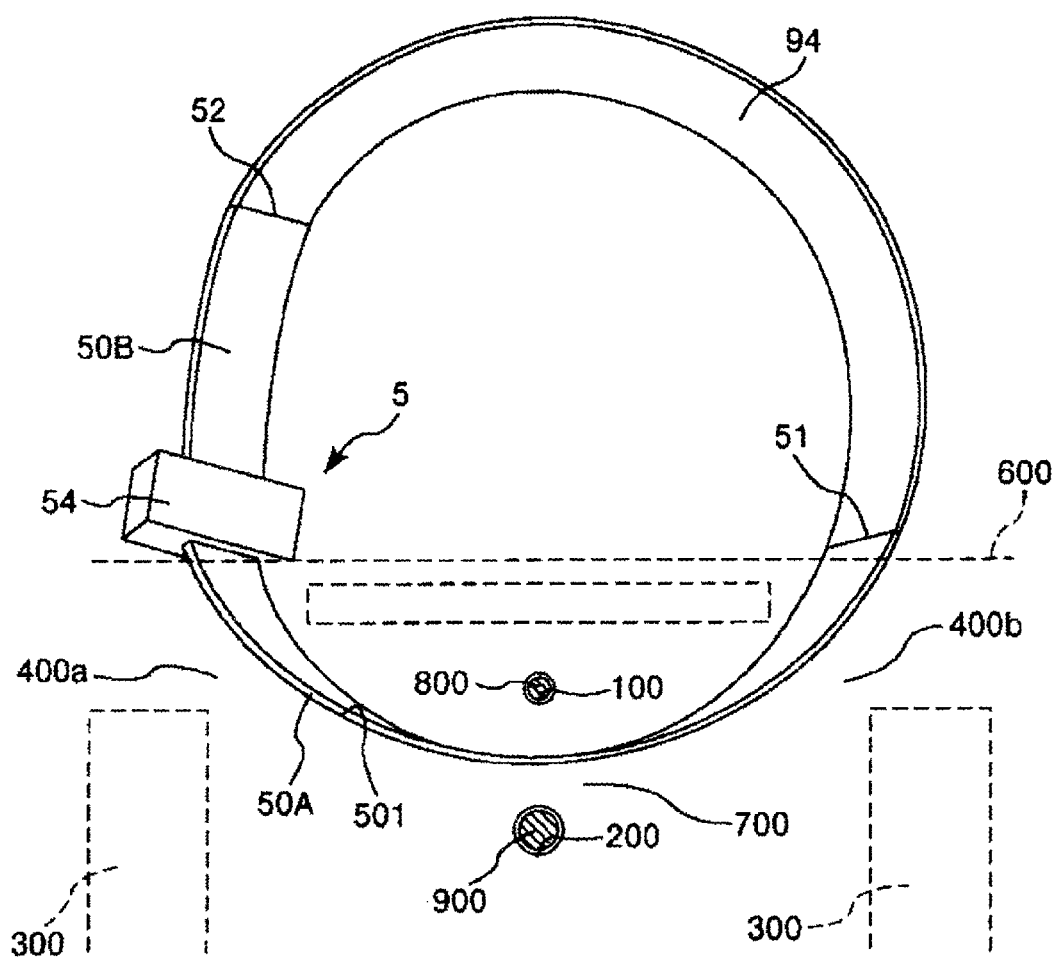
FIG. 24 is a view illustrating a manner of use of a medical device according to an eighth exemplary embodiment of the present disclosure.

FIG. 24 is a view illustrating a manner of use of a medical device according to an eighth exemplary embodiment of the present disclosure.

In the following, the medical device according to the eighth embodiment of the present disclosure is described with reference to FIG. 24. However, the description is given principally of differences of the eighth embodiment from the embodiments described hereinabove and description of like matters is omitted herein to avoid redundancy.

The medical device of the present embodiment is similar to that of the sixth exemplary embodiment described hereinabove except that it is different in configuration (shape) of the guide member.

As depicted in FIG. 24, the guide member 9 in the present embodiment is configured from a stylet (member) 94 which is hard and elongated and is curved in the same direction as that of the curved portion of the puncture needle 31. The stylet 94 is inserted at a proximal end portion thereof into the distal end opening 51 of the inner tube 50A and is inserted at a distal end portion thereof into the proximal end opening 52 of the outer tube 50B when it is used. Consequently, the inner tube 50A can be pulled out from within the living body by a simple operation of pulling the inner tube 50A to the upper side in FIG. 24 along the shape of the stylet 94.

Figure 25:
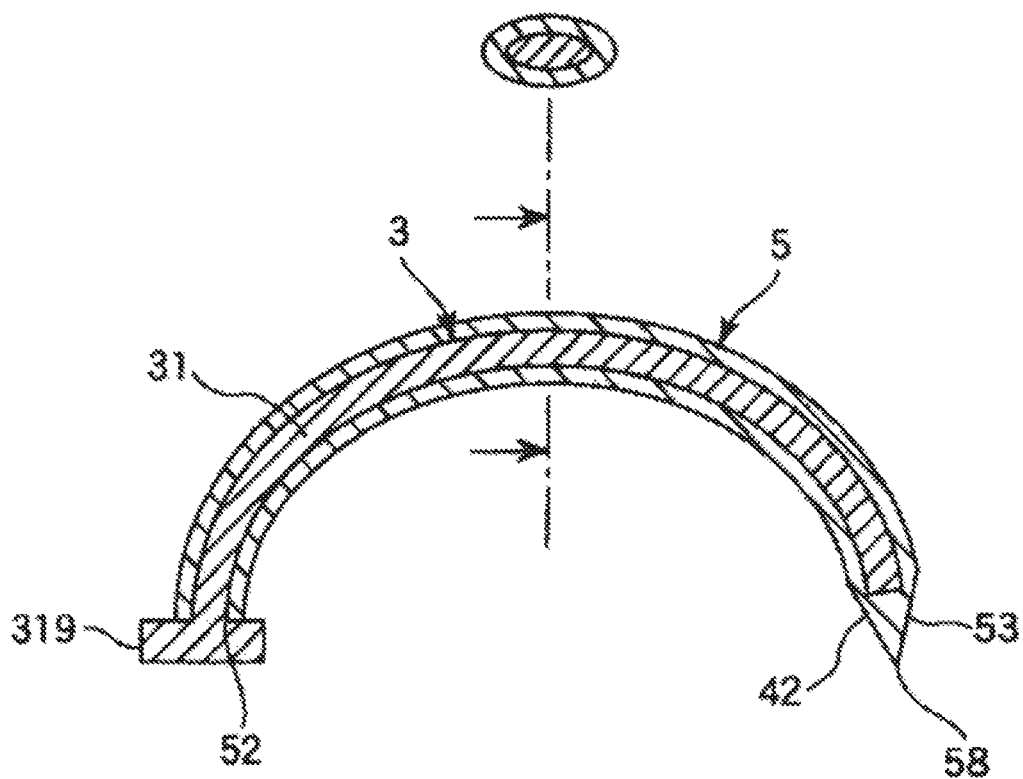
FIG. 25 is a cross sectional view of a medical tube provided in a medical device according to a ninth exemplary embodiment of the present disclosure.

FIG. 25 is a cross sectional view of a medical tube provided in a medical device according to a ninth exemplary embodiment of the present disclosure.

In the following, the medical device according to the ninth exemplary embodiment of the present disclosure is described with reference to FIG. 25. However, the description is given principally of differences of the ninth exemplary embodiment from the embodiments described hereinabove and description of like matters is omitted herein to avoid redundancy.

The medical device of the present embodiment is similar to that of the sixth exemplary embodiment described hereinabove except that it is different in the configuration (shape) of the medical tube.

As depicted in FIG. 25, in the present embodiment, the distal end of the sheath 5 is closed up and forms a sharp needle tip 58. By the needle tip 58, the living body can be punctured with relative certainty. In this manner, the needle tip 58 functions as a puncture portion for puncturing the living body.

It is to be noted that, in the case of the present embodiment, the needle tip 315 can be omitted from the puncture needle 31 of the puncture member 3. Such a puncture needle 31 as just described functions as a stylet, which reinforces the sheath 5 from the inner side.

Figure 26:
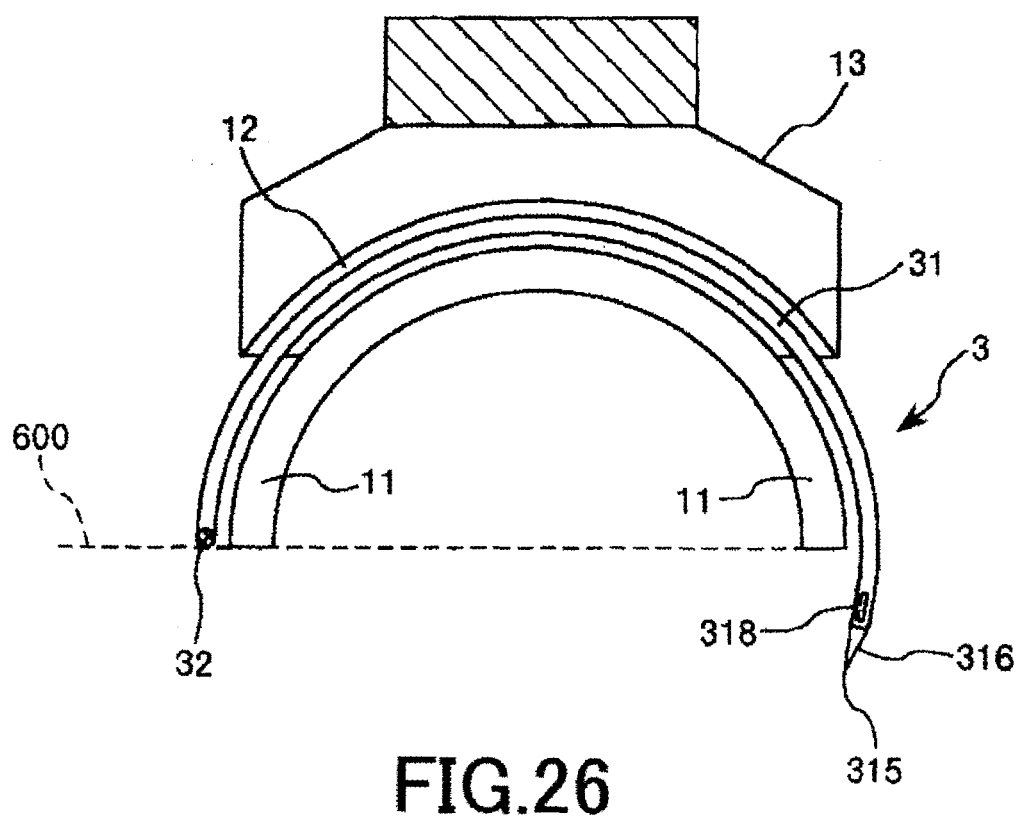
FIGS. 26 and 27 are cross sectional views illustrating a manner of use of a medical device according to a tenth exemplary embodiment of the present disclosure.
Figure 27:
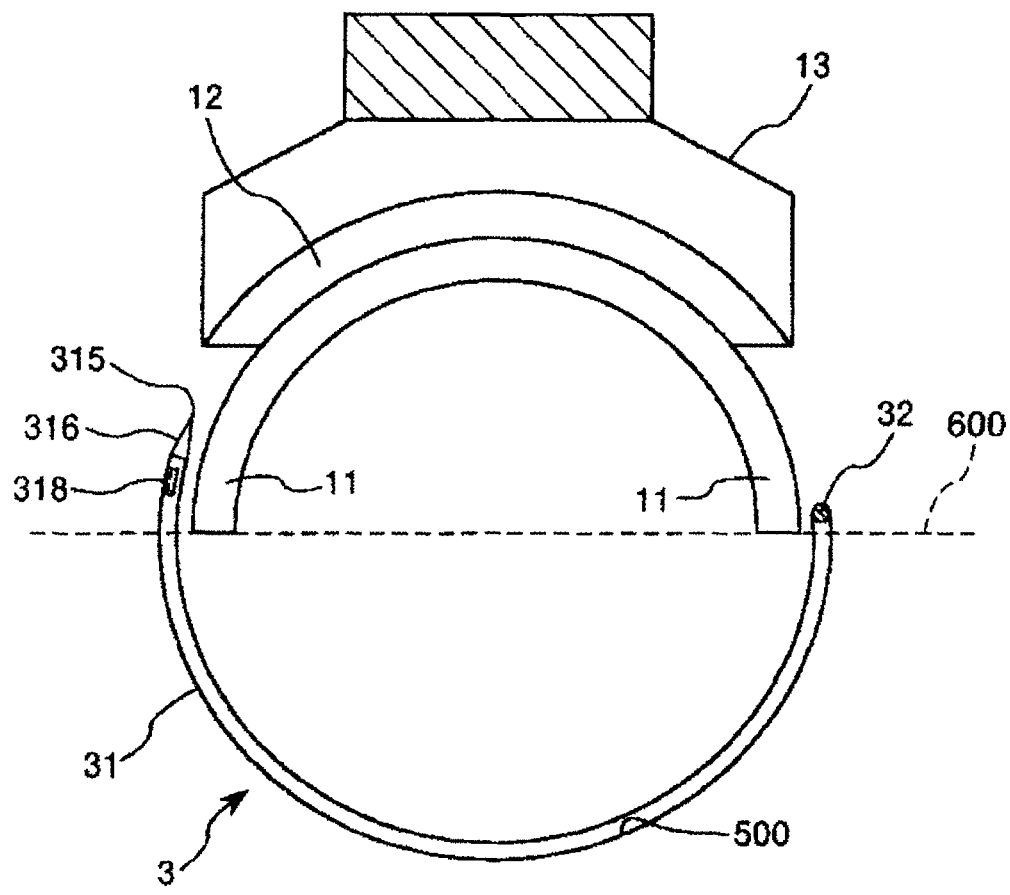

FIGS. 26 and 27 are views illustrating a manner of use of a medical device according to a tenth exemplary embodiment of the present disclosure.

In the following, the medical device according to the tenth exemplary embodiment of the present disclosure is described with reference to FIGS. 26 and 27. However, the description is given principally of differences of the tenth exemplary embodiment from the embodiments described hereinabove and description of like matters is omitted herein to avoid redundancy.

The medical device of the present embodiment is similar to that of the first exemplary embodiment described hereinabove except that it is different in configuration (shape) of the pressing member.

The medical device 1 of the present embodiment can include a pressing member 13 on which a guide groove 12 for guiding the puncture needle 31 and projections 11 which press, when the puncture member 3 is inserted into the biological tissue 700, portions in the proximity of the living body surface 600, through which the puncture member 3 passes, toward the biological tissue 700 side.

The guide groove 12 is a groove which has a substantially C shape and into which the puncture needle 31 is inserted. Consequently, puncture (insertion) of the puncture needle 31 can be accurately and easily carried out. The overall length of the guide groove 12 is smaller than the overall length of the puncture needle 31, and in an initial state, the needle tip of the puncture needle 31 projects from the proximal end of the guide groove 12 while the needle tip 315 of the puncture needle 31 projects from the distal end of the guide groove 12.

Further, in a region positioned on the inner side with respect to the guide groove 12 (puncture needle 31), a pair of projections 11 are formed such that they project to the lower side. Each of the projections 11 extends in an arc along the curved portion of the puncture needle 31. Further, each projection 11 continues to the guide groove 12. In the initial state, the needle tip 315 of the puncture needle 31 is positioned on the lower side than a lower face of the projections 11, and the proximal end of the puncture needle 31 is positioned at a substantially same height as the lower face of the projections 11. If the puncture needle 31 is turned from the initial state depicted in FIG. 26, then the pressing member 13 projects further from the guide groove 12 into a state depicted in FIG. 27. It is to be noted that, depending upon the length or the like of the projections 11, the needle tip of the puncture needle 31 may be positioned at the same height as the lower face of the projections 11 or may be positioned on the upper side with respect to the lower face.

With such a pressing member 13 as described above, for example, where the patient has a subcutaneous tissue of a comparatively great thickness, the projections 11 can be sunk into the living body to allow the puncture needle 31 to puncture more deeply by pressing the projections 11 against the living body surface 600. Therefore, the medical device 1 of the present embodiment can cope with a patient having a comparatively thick subcutaneous tissue or a like patient.

The medical device of the present disclosure has been described based on the embodiments depicted in the drawings. However, the present disclosure is not limited to them, and the configuration of the components can be replaced by elements of an arbitrary configuration which have similar functions. Further, the medical device may have an arbitrary component added thereto.

Further, in the medical device of the present disclosure, both of the puncture needle and the sheath are configured such that they have a restriction mechanism for restricting rotation of the sheath. However, the present disclosure is not limited to this, and the medical device may be configured, for example, such that one of the puncture needle and the sheath has a restriction mechanism.

Further, the puncture needle of the puncture member must only have a curved portion at least at part thereof and may be configured such that, for example, the puncture needle is entirely curved in an elliptical shape or has, only at part thereof, a portion which is curved in an elliptical shape. In accordance with an exemplary embodiment, for example, the puncture needle may have, at least at part thereof, a portion curved in an elliptical shape.

Further, while, in the medical devices of the embodiments, the vaginal insertion portion functions as an auxiliary insertion portion, the present disclosure is not limited to this but the medical device may be configured such that the urethral insertion portion functions as an auxiliary insertion portion.

Further, in the foregoing description, the medical device is applied to a device which is used when an embeddable implant for the medical treatment of urinary incontinence of a female is embedded into a living body. However, the application of the medical device is not limited to this.

For example, the present disclosure has an application target including excretion failure (such as urinary urgency, frequent urination, urinary incontinence, fecal incontinence, urinary retention and difficulty in urination), pelvic floor disorders including pelvic organ prolapse, vesicovaginal fistula, urethra vaginal fistula, pelvic pain and so forth, which are caused by weakening of the pelvic floor muscles. The pelvic organ prolapse can include such diseases as cystocele, small intestine aneurysm, rectocele and uterine prolapse. Alternatively, the pelvic organ prolapse can include such diseases as forward vaginal wall prolapse, rearward vaginal wall prolapse, vaginal apical prolapse and vaginal vault prolapse which are ways to call classified depending upon the prolapsed vaginal wall region.

Further, the hypermobility organizations include the bladder, the vagina, the uterus, intestines and so forth. The fine-moving organizations include bones, muscles, fascias, ligaments and so forth. Especially, in the pelvic floor disorders, obturator fasciae, coccyx fasciae, ligamentum cardinale, sacrum uterus ligaments, sacrospinous ligaments and so forth are included.

The manipulations for connecting a hypermobility organization to a fine-moving organization in pelvic floor diseases include a retropubic sling surgery, a transobturator sling surgery (transobturator tape (TOT) surgery), a tension-free vaginal mesh (TVM) surgery, a uterosacral ligament suspension (USLS) surgery, a sacrospinous ligament fixation (SSLF) surgery, an iliococcygeus fascia fixation surgery, a coccygeus fascia fixation surgery, and the like.

According to the present disclosure, a medical device can include an insertion portion configured to be inserted into a biological lumen, an elongated body provided for movement and configured to pass a biological tissue, a supporting member configured to support the elongated body for movement thereon and support the insertion portion thereon, a dissection portion configured to dissect, when the elongated body moves, the biological tissue in accordance with the movement of the elongated body, and a restriction mechanism configured to restrict the dissecting portion such that a direction in which the dissection portion dissects the biological tissue is fixed with respect to the insertion portion. Consequently, when an elongated implant is to be embedded into a living body such that it is directed in the predetermined direction, the embedding operation can be carried out readily and with certainty, and the burden on the patient is light. Further, the safety of the patient is high and also the safety of the operator is high.

For example, where the medical device of the present disclosure is used for treatment of urinary incontinence of a female, when an elongated implant for treatment of urinary incontinence is to be embedded, incision of the vaginal wall is unnecessary, and the implant can be embedded by a manipulation of low invasion. Further, such a situation that the implant is exposed to the inside of the vagina through a wound caused by incision as in the case in which the vaginal wall is incised or that such complications as infection from the wound or the like are caused can be prevented. This is very safe, and the implant can be embedded with certainty.

For example, since the biological tissue can be dissected with a predetermined width by the dissection portion, the implant can be embedded with certainty by a manipulation of very low invasion.

Further, the puncture needle and the connector (dissection portion) can be connected to each other such that the positional relationship of the puncture needle and the connector in the rotational direction around the axis is fixed. Further, in this connection state, rotation of the connector around the axis with respect to the puncture needle is restricted. Therefore, the implant can be embedded such that the direction thereof is fixed with respect to the insertion portion.

Further, since the operator need not carry out incision or the like, the fingertip of the operator can be prevented from being injured or damaged by a knife.

The detailed description above describes a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device, comprising:
   an insertion portion configured to be inserted into a biological lumen;
   an elongated body provided for movement about an axis and configured to pass a biological tissue;
   a supporting member configured to support the elongated body for the movement about the axis and configured to support the insertion portion;
   a dissection portion configured to dissect, when the elongated body moves, the biological tissue in accordance with the movement of the elongated body; and
   a restriction mechanism configured to restrict the dissecting portion such that a direction in which the dissection portion dissects the biological tissue is fixed with respect to the insertion portion.

2. The medical device according to claim 1, wherein the direction in which the dissection portion dissects the biological tissue is parallel at least part thereof to the insertion portion.

3. The medical device according to claim 2, wherein the insertion portion is a urethral insertion portion configured to be inserted into a urethra;
  the elongated body is disposed for turning motion; and
  a direction in which the dissection portion dissects when the biological tissue on the remote side of the urethral insertion portion with respect to a center axis of turning motion of the elongated member is to be dissected is a parallel direction to the urethral insertion portion.

4. The medical device according to claim 2, wherein the insertion portion includes a urethral insertion portion configured for insertion into the urethra and a vaginal insertion portion configured for insertion into a vagina;
  the elongated body is disposed for turning motion; and
  a direction in which the dissection portion dissects when the biological tissue on a near side of the vaginal insertion portion with respect to a center axis of turning motion of the elongated member is to be dissected is a parallel direction to the urethral insertion portion.

5. The medical device according to claim 1, wherein the insertion portion has a first insertion portion and a second insertion portion configured to be inserted into two biological lumens positioned adjacent each other with the biological tissue interposed between the two biological lumens; and
  a direction in which the dissection portion dissects the biological tissue between the first insertion portion and the second insertion portion is a parallel direction to at least one of the first insertion portion and the second insertion portion.

6. The medical device according to claim 5, wherein the first insertion portion is a urethral insertion portion configured for insertion into the urethra;
  the second insertion portion is a vaginal insertion portion configured for insertion into the vagina; and
  the direction in which the dissection portion dissects the biological tissue between the urethral insertion portion and the vaginal insertion portion is a parallel direction to at least one of the urethral insertion portion and the vaginal insertion portion.

7. The medical device according to claim 1, comprising:
  a medical tube configured to be inserted into the biological tissue in an assembled state in which the medical tube is inserted in and assembled to the elongated body.

8. The medical device according to claim 7, wherein the medical tube and the elongated body have, at least at part thereof in a longitudinal direction, a flattened portion having a flattened transverse sectional shape such that the flattened portions of the medical tube and the elongated body in the assembled state overlap with each other to exhibit a function as the restriction mechanism.

9. The medical device according to claim 7, wherein the medical tube has, at a distal end portion thereof, a needle tip portion configured to puncture the biological tissue.

10. The medical device according to claim 1, comprising:
  a medical tube having an elongated shape and configured to be inserted into a living body; and
  a guide member configured to guide the medical tube when the medical tube is to be pulled from the biological tissue.

11. The medical device according to claim 10, A medical device, comprising:
  an insertion portion configured to be inserted into a biological lumen;
  an elongated body provided for movement and configured to pass a biological tissue;
  a supporting member configured to support the elongated body for movement on the supporting member and support the insertion portion on the supporting member;
  a dissection portion configured to dissect, when the elongated body moves, the biological tissue in accordance with the movement of the elongated body;
  a restriction mechanism configured to restrict the dissecting portion such that a direction in which the dissection portion dissects the biological tissue is fixed with respect to the insertion portion;
  a medical tube having an elongated shape and configured to be inserted into a living body, wherein the elongated body has a curved portion curved in an arc; and
  a guide member configured to guide the medical tube when the medical tube is to be pulled from the biological tissue, the guide member has a curved face which has a curved face curved in a direction same as the curved portion of the elongated body and is configured to abut with the medical tube.

12. The medical device according to claim 11, wherein the elongated body has a curved portion curved in an arc;
  the medical tube has an end opening open to a distal end thereof; and
  the guide member has an elongated shape curved in a direction same as a direction of the curved portion and is configured at a distal end portion thereof from a hard member configured to be inserted into the end opening.

13. The medical device according to claim 11, wherein the direction in which the dissection portion dissects the biological tissue is parallel at least part thereof to the insertion portion.

14. The medical device according to claim 13, wherein the insertion portion is a urethral insertion portion configured to be inserted into a urethra;
  the elongated body is disposed for turning motion; and
  a direction in which the dissection portion dissects when the biological tissue on the remote side of the urethral insertion portion with respect to a center axis of turning motion of the elongated member is to be dissected is a parallel direction to the urethral insertion portion.

15. The medical device according to claim 13, wherein the insertion portion includes a urethral insertion portion configured for insertion into the urethra and a vaginal insertion portion configured for insertion into a vagina;
  the elongated body is disposed for turning motion; and
  a direction in which the dissection portion dissects when the biological tissue on a near side of the vaginal insertion portion with respect to a center axis of turning motion of the elongated member is to be dissected is a parallel direction to the urethral insertion portion.

16. The medical device according to claim 11, wherein the insertion portion has a first insertion portion and a second insertion portion configured to be inserted into two biological lumens positioned adjacent each other with the biological tissue interposed between the two biological lumens; and
  a direction in which the dissection portion dissects the biological tissue between the first insertion portion and the second insertion portion is a parallel direction to at least one of the first insertion portion and the second insertion portion.

17. The medical device according to claim 16, wherein the first insertion portion is a urethral insertion portion configured for insertion into the urethra;
  the second insertion portion is a vaginal insertion portion configured for insertion into the vagina; and the direction in which the dissection portion dissects the biological tissue between the urethral insertion portion and the vaginal insertion portion is a parallel direction to at least one of the urethral insertion portion and the vaginal insertion portion.

18. A method of forming a path in biological tissue, the method comprising:
   inserting an insertion portion into a biological lumen;
   moving an elongated body about an axis and past a biological tissue;
   supporting the elongated body and the insertion portion on a supporting member, the supporting member configured to support the elongated body for the movement about the axis;
   dissecting, when the elongated body moves, the biological tissue in accordance with the movement of the elongated body with a dissection portion; and
   restricting the dissecting portion such that a direction in which the dissection portion dissects the biological tissue is fixed with respect to the insertion portion.

19. The method according to claim 18,
   wherein the direction in which the dissection portion dissects the biological tissue is parallel at least part thereof to the insertion portion.

20. The method according to claim 19, comprising:
   inserting the insertion portion into a urethra;
   turning the elongated body; and
   a direction in which the dissection portion dissects when the biological tissue on the remote side of the insertion portion with respect to a center axis of turning motion of the elongated member is to be dissected is a parallel direction to the insertion portion.

* * * * *